(12) United States Patent
Swanson et al.

(10) Patent No.: US 10,035,855 B2
(45) Date of Patent: Jul. 31, 2018

(54) ANTIBODY THERAPEUTICS THAT BIND CD47

(71) Applicant: Sorrento Therapeutics, Inc., San Diego, CA (US)

(72) Inventors: Barbara A. Swanson, Encinitas, CA (US); John Dixon Gray, San Diego, CA (US); Heyue Zhou, San Diego, CA (US)

(73) Assignee: SORRENTO THERAPEUTICS, INC., San Diego, CA (US)

( * ) Notice: Subject to any disclaimer, the term of this patent is extended or adjusted under 35 U.S.C. 154(b) by 7 days.

(21) Appl. No.: 15/061,771

(22) Filed: Mar. 4, 2016

(65) Prior Publication Data

US 2016/0257751 A1 Sep. 8, 2016

Related U.S. Application Data

(60) Provisional application No. 62/128,462, filed on Mar. 4, 2015.

(51) Int. Cl.
| | | |
|---|---|---|
| *A61K 39/395* | (2006.01) | |
| *C07K 16/28* | (2006.01) | |
| *C07K 16/30* | (2006.01) | |

(52) U.S. Cl.
CPC .......... *C07K 16/2803* (2013.01); *C07K 16/30* (2013.01); *C07K 2317/21* (2013.01); *C07K 2317/56* (2013.01); *C07K 2317/565* (2013.01); *C07K 2317/567* (2013.01); *C07K 2317/76* (2013.01); *C07K 2317/90* (2013.01); *C07K 2317/92* (2013.01)

(58) Field of Classification Search
None
See application file for complete search history.

(56) References Cited

PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
White et al. (2001, Ann. Rev. Med., 2001, 52:125-145).*
Meibohm (Pharmacokinetics and Pharmacodynamics of Biotech Drugs, Wiley-VHC, 2006, chapter 3, p. 45-91).*
International Search Report for PCT/US2016/020980, published Sep. 9, 2016, 5 pages.

* cited by examiner

*Primary Examiner* — Laura B Goddard
*Assistant Examiner* — Meera Natarajan
(74) *Attorney, Agent, or Firm* — Danielle L. Herritt; Cristin H. Cowles; Womble Bond Dickinson (US) LLP

(57) ABSTRACT

There is disclosed compositions and methods relating to or derived from anti-CD47 antibodies. More specifically, there is disclosed fully human antibodies that bind CD47, CD47-antibody binding fragments and derivatives of such antibodies, and CD47-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating a disease.

15 Claims, 4 Drawing Sheets

SEQUENCE LISTING

<160> NUMBER OF SEQ ID NOS: 32

<210> SEQ ID NO 1
<211> LENGTH: 119
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Leu Trp Phe Ser Glu Phe Asp Tyr Trp Gly Gln Gly
            100                 105                 110

Thr Leu Val Thr Val Ser Ser
            115

<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ser Val Leu Thr Gln Pro Ser Ser Val Ser Ala Ser Pro Gly Gln
1               5                   10                  15

Ser Ile Thr Ile Ser Cys Ser Gly Thr Ser Ser Asp Val Gly Gly His
                20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
        50                  55                  60

Ser Gly Ser Lys Ser Gly Asn Thr Ala Ser Leu Thr Ser Gly Leu
65                  70                  75                  80

Gln Ala Glu Asp Glu Ala Asp Tyr Tyr Cys Cys Ser Tyr Ala Gly Ser
                85                  90                  95

Arg Val Tyr Val Phe Gly Thr Gly Thr Lys Leu Thr Val Leu
            100                 105                 110

<210> SEQ ID NO 3
<211> LENGTH: 4
<212> TYPE: PRT
<213> ORGANISM: Unknown
<220> FEATURE:
<223> OTHER INFORMATION: Description of Unknown:
      Hinge region sequence

<400> SEQUENCE: 3

Cys Pro Ser Cys
1

<210> SEQ ID NO 4
<211> LENGTH: 110
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ser Val Leu Thr Gln Pro Ala Ser Val Ser Gly Ser Pro Gly Gln
1               5                   10                  15

Ser Ile Ser Ile Ser Cys Thr Gly Thr Ser Ser Asp Val Gly Gly His
            20                  25                  30

Asn Tyr Val Ser Trp Tyr Gln Gln His Pro Gly Lys Ala Pro Lys Leu
        35                  40                  45

Met Ile Tyr Asp Val Arg Asn Arg Pro Ser Gly Val Ser Asn Arg Phe
    50                  55                  60

Ser Gly Ser Lys Ser Gly Ser Thr Ala Ser Leu Thr Ile Ser Gly Leu
65                  70                  75                  80

Gln Thr Glu Asp Glu Ala Asp Tyr Tyr Cys Asn Ser Tyr Thr Gly Ser
                85                  90                  95

Arg Thr Tyr Val Phe Gly Ser Gly Thr Lys Leu Thr Val Leu
            100                 105                 110

<210> SEQ ID NO 5
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Ser Ala Leu Thr Gln Pro Ala Ser Val Ser Gly Ser Pro Gly Gln
1               5                   10                  15

Ser Ile Ser Ile Ser Cys Thr Gly Thr Ser Val Asp Val Gly Gly His
            20                  25                  30

Asn Tyr Val Ser Trp Tyr Gln Gln His Pro Gly Lys Ala Pro Lys Leu
        35                  40                  45

Met Ile Tyr Asp Val Arg Asn Arg Pro Ser Gly Val Ser Asn Arg Phe
    50                  55                  60

Ser Gly Ser Lys Ser Gly Ser Thr Ala Ser Leu Thr Ile Ser Gly Leu
65                  70                  75                  80

Gln Thr Glu Asp Glu Ala Asp Tyr Tyr Cys Asn Ser Tyr Thr Gly Ser
                85                  90                  95

Arg Thr Tyr Val Phe Gly Ser Gly Thr Lys Leu Thr Val Leu
            100                 105                 110

<210> SEQ ID NO 6
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ser Ala Leu Thr Gln Pro Ala Ser Val Ser Gly Ser Pro Gly Gln
1               5                   10                  15

Ser Ile Ser Ile Ser Cys Thr Gly Thr Ser Ser Asp Val Gly Gly His
            20                  25                  30

Asn Tyr Val Ser Trp Tyr Gln Gln His Pro Gly Lys Ala Pro Lys Leu
```

```
                35                  40                  45
Met Ile Tyr Asp Val Arg Asn Arg Pro Ser Gly Val Ser Asn Arg Phe
    50                  55                  60

Ser Gly Ser Lys Ser Gly Ser Thr Ala Ser Leu Thr Ile Ser Gly Leu
65                  70                  75                  80

Gln Thr Glu Asp Glu Ala Asp Tyr Tyr Cys Leu Ser Tyr Thr Gly Ser
                85                  90                  95

Arg Thr Tyr Val Phe Gly Ser Gly Thr Lys Leu Thr Val Leu
            100                 105                 110

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Leu Trp Phe Ser Glu Phe Asp Tyr Trp Gly Gln Gly
            100                 105                 110

Thr Leu Val Thr Val Ser Ser
        115

<210> SEQ ID NO 8
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Ser Ala Leu Thr Gln Pro Ala Ser Val Ser Gly Ser Pro Gly Gln
1               5                   10                  15

Ser Ile Ser Ile Ser Cys Thr Gly Thr Ser Ser Asp Val Gly Gly His
            20                  25                  30

Asn Tyr Val Ser Trp Tyr Gln Gln His Pro Gly Lys Ala Pro Lys Leu
        35                  40                  45

Met Ile Tyr Asp Val Arg Asn Arg Pro Ser Gly Val Ser Asn Arg Phe
    50                  55                  60

Ser Gly Ser Lys Ser Gly Ser Thr Ala Ser Leu Thr Ile Ser Gly Leu
65                  70                  75                  80

Gln Thr Glu Asp Glu Ala Asp Tyr Tyr Cys Asn Ser Tyr Thr Gly Ser
                85                  90                  95

Arg Thr Tyr Val Phe Gly Ser Gly Thr Lys Leu Thr Val Leu
```

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Lys Leu Trp Phe Ser Glu Phe Asp Tyr Trp Gly Gln Gly
                100                 105                 110

Thr Leu Val Thr Val Ser Ser
            115

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Leu Trp Tyr Ser Glu Phe Asp Tyr Trp Gly Gln Gly
                100                 105                 110

Thr Leu Val Thr Val Ser Ser
            115

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Leu Trp Phe Thr Glu Phe Asp Tyr Trp Gly Gln Gly
            100                 105                 110

Thr Leu Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Leu Trp Phe Ser Ala Phe Asp Tyr Trp Gly Gln Gly
            100                 105                 110

Thr Leu Val Thr Val Ser Ser
        115

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

```
Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Leu Trp Phe Ser Ser Phe Asp Tyr Trp Gly Gln Gly
            100                 105                 110

Thr Leu Val Thr Val Ser Ser
        115
```

```
<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Leu Trp Tyr Thr Glu Phe Asp Tyr Trp Gly Gln Gly
            100                 105                 110

Thr Leu Val Thr Val Ser Ser
        115
```

```
<210> SEQ ID NO 15
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15
```

```
Gln Ser Ala Leu Thr Gln Pro Ala Ser Val Ser Gly Ser Pro Gly Gln
1               5                   10                  15

Ser Ile Ser Ile Ser Cys Thr Gly Thr Ser Val Asp Val Gly Gly His
            20                  25                  30

Asn Tyr Val Ser Trp Tyr Gln Gln His Pro Gly Lys Ala Pro Lys Leu
            35                  40                  45

Met Ile Tyr Asp Val Arg Asn Arg Pro Ser Gly Val Ser Asn Arg Phe
        50                  55                  60

Ser Gly Ser Lys Ser Gly Ser Thr Ala Ser Leu Thr Ile Ser Gly Leu
65                  70                  75                  80
```

```
Gln Thr Glu Asp Glu Ala Asp Tyr Tyr Cys Leu Ser Tyr Thr Gly Ser
                85                  90                  95

Arg Thr Tyr Val Phe Gly Ser Gly Thr Lys Leu Thr Val Leu
            100                 105                 110

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Leu Trp Tyr Thr Ala Phe Asp Tyr Trp Gly Gln Gly
            100                 105                 110

Thr Leu Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Lys Leu Trp Tyr Thr Glu Phe Asp Tyr Trp Gly Gln Gly
            100                 105                 110

Thr Leu Val Thr Val Ser Ser
        115

<210> SEQ ID NO 18
```

<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Leu Trp Tyr Ser Glu Phe Asp Tyr Trp Gly Gln Gly
            100                 105                 110

Thr Leu Val Thr Val Ser Ser
        115

<210> SEQ ID NO 19
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Leu Thr Gln Ser Pro Ser Thr Leu Ser Ala Ser Val Gly
1               5                   10                  15

Asp Arg Val Thr Ile Thr Cys Arg Ala Thr Gln Thr Thr Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Asp Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Gly Phe Arg Met
                85                  90                  95

Tyr Thr Phe Gly Gln Gly Thr Lys Leu Glu Ile Lys
            100                 105

<210> SEQ ID NO 20
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Thr Pro Ser Ser Leu Ser Ala Ser Val Gly
1               5                   10                  15

```
Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Gly Phe Arg Met
                85                  90                  95

Tyr Thr Phe Gly Gln Gly Thr Lys Val Glu Ile Lys
            100                 105

<210> SEQ ID NO 21
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Lys
            20                  25                  30

Asn Gly Asn Asn Tyr Leu Asp Trp Tyr Leu Gln Arg Pro Gly Gln Ser
        35                  40                  45

Pro Gln Leu Leu Ile Tyr Leu Ala Ser Asn Arg Ala Ser Gly Val Pro
50                  55                  60

Asp Arg Phe Ser Gly Ser Gly Ser Gly Thr Asp Phe Thr Leu Glu Ile
65                  70                  75                  80

Ser Arg Val Gln Pro Glu Asp Val Gly Val Tyr Tyr Cys Met Arg Gly
                85                  90                  95

Leu Gln Thr Pro Thr Phe Gly Pro Gly Thr Lys Val Asp Ile Lys
            100                 105                 110

<210> SEQ ID NO 22
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Ser Thr Leu Trp Val Ser Glu Phe Asp Tyr Trp Gly Gln Gly
            100                 105                 110

Thr Leu Val Thr Val Ser Ser
        115

<210> SEQ ID NO 23
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Ser Ala Leu Thr Gln Pro Ala Ser Val Ser Gly Ser Pro Gly Gln
1               5                   10                  15

Ser Ile Ser Ile Ser Cys Thr Gly Thr Ser Ser Asp Val Gly Trp His
            20                  25                  30

Asn Tyr Val Ser Trp Tyr Gln Gln His Pro Gly Lys Ala Pro Lys Leu
        35                  40                  45

Met Ile Tyr Asp Val Arg Asn Arg Pro Ser Gly Val Ser Asn Arg Phe
    50                  55                  60

Ser Gly Ser Lys Ser Gly Ser Thr Ala Ser Leu Thr Ile Ser Gly Leu
65                  70                  75                  80

Gln Thr Glu Asp Glu Ala Asp Tyr Tyr Cys Asn Ser Tyr Thr Gly Ser
                85                  90                  95

Arg Thr Tyr Val Phe Gly Ser Gly Thr Lys Leu Thr Val Leu
            100                 105                 110

<210> SEQ ID NO 24
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Leu Trp Phe Ser Glu Phe Asp Trp Trp Gly Gln Gly
            100                 105                 110

Thr Leu Val Thr Val Ser Ser
        115

<210> SEQ ID NO 25
<211> LENGTH: 110
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 25

Gln Ser Ala Leu Thr Gln Pro Ala Ser Val Ser Gly Ser Pro Gly Gln
1               5                   10                  15

Ser Ile Ser Ile Ser Cys Thr Gly Thr Ser Ser Asp Val Val Gly His
            20                  25                  30

Asn Tyr Val Ser Trp Tyr Gln Gln His Pro Gly Lys Ala Pro Lys Leu
        35                  40                  45

Met Ile Tyr Asp Val Arg Asn Arg Pro Ser Gly Val Ser Asn Arg Phe
    50                  55                  60

Ser Gly Ser Lys Ser Gly Ser Thr Ala Ser Leu Thr Ile Ser Gly Leu
65                  70                  75                  80

Gln Thr Glu Asp Glu Ala Asp Tyr Tyr Cys Asn Ser Tyr Thr Gly Ser
                85                  90                  95

Arg Thr Tyr Val Phe Gly Ser Gly Thr Lys Leu Thr Val Leu
            100                 105                 110

<210> SEQ ID NO 26
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Ser Ala Leu Thr Gln Pro Ala Ser Val Ser Gly Ser Pro Gly Gln
1               5                   10                  15

Ser Ile Ser Ile Ser Cys Thr Gly Thr Ser Ser Asp Val Gly Gly His
            20                  25                  30

Asn Tyr Val Ser Trp Tyr Gln Gln His Pro Gly Lys Ala Pro Lys Leu
        35                  40                  45

Met Ile Tyr Asp Val Arg Asn Arg Pro Ser Gly Val Ser Asn Arg Phe
    50                  55                  60

Ser Gly Ser Lys Ser Gly Ser Thr Ala Ser Leu Thr Ile Ser Gly Leu
65                  70                  75                  80

Gln Thr Glu Asp Glu Ala Asp Tyr Tyr Cys Thr Ser Tyr Thr Gly Ser
                85                  90                  95

Arg Thr Tyr Val Phe Gly Ser Gly Thr Lys Leu Thr Val Leu
            100                 105                 110

<210> SEQ ID NO 27
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Ser Val Leu Thr Gln Pro Ser Ser Val Ser Ala Ser Pro Gly Gln
1               5                   10                  15

Ser Ile Thr Ile Ser Cys Ser Gly Thr Ser Ser Asp Val Gly Gly His
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe

```
                    50                  55                  60
Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ala Ser Tyr Ala Gly Ser
                 85                  90                  95

Arg Val Tyr Val Phe Gly Thr Gly Thr Lys Leu Thr Val Leu
                100                 105                 110

<210> SEQ ID NO 28
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Ser Val Leu Thr Gln Pro Ser Ser Val Ser Ala Ser Pro Gly Gln
 1               5                  10                  15

Ser Ile Thr Ile Ser Cys Ser Gly Thr Ser Ser Asp Val Gly Gly His
                 20                  25                  30

Asn Tyr Val Ser Trp Tyr Gln Gln His Pro Gly Lys Ala Pro Lys Leu
             35                  40                  45

Met Ile Tyr Asp Val Thr Lys Arg Pro Ser Gly Val Pro Asp Arg Phe
         50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Leu Ser Tyr Ala Gly Ser
                 85                  90                  95

Arg Val Tyr Val Phe Gly Thr Gly Thr Lys Leu Thr Val Leu
                100                 105                 110

<210> SEQ ID NO 29
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Ser Val Leu Thr Gln Pro Ser Ser Val Ser Ala Ser Pro Gly Gln
 1               5                  10                  15

Ser Ile Thr Ile Ser Cys Ser Gly Thr Ser Ser Asp Val Gly Gly His
                 20                  25                  30

Asn Tyr Val Ser Trp Tyr Gln Gln His Pro Gly Lys Ala Pro Lys Leu
             35                  40                  45

Met Ile Tyr Asp Val Thr Lys Arg Pro Ser Gly Val Pro Asp Arg Phe
         50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Gln Ser Tyr Ala Gly Ser
                 85                  90                  95

Arg Val Tyr Val Phe Gly Thr Gly Thr Lys Leu Thr Val Leu
                100                 105                 110

<210> SEQ ID NO 30
<211> LENGTH: 110
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 30

Gln Ser Val Leu Thr Gln Pro Ser Ser Val Ser Ala Ser Pro Gly Gln
1               5                   10                  15

Ser Ile Thr Ile Ser Cys Ser Gly Thr Ser Ser Asp Val Gly Gly His
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Arg Val Tyr Val Phe Gly Thr Gly Thr Lys Leu Thr Val Leu
            100                 105                 110

<210> SEQ ID NO 31
<211> LENGTH: 4
<212> TYPE: PRT
<213> ORGANISM: Unknown
<220> FEATURE:
<223> OTHER INFORMATION: Description of Unknown:
      Hinge region sequence

<400> SEQUENCE: 31

Cys Pro Pro Cys
1

<210> SEQ ID NO 32
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Lys Leu Trp Tyr Thr Ala Phe Asp Tyr Trp Gly Gln Gly
            100                 105                 110

Thr Leu Val Thr Val Ser Ser
        115

ANTIBODY THERAPEUTICS THAT BIND CD47

RELATED APPLICATIONS

This application claims priority to U.S. Provisional Application No. 62/128,462, filed on Mar. 4, 2015, the entire contents of which are incorporated by reference in their entirety herein.

SEQUENCE LISTING

The instant application contains a Sequence Listing which has been submitted electronically in ASCII format and is hereby incorporated by reference in its entirety. Said ASCII copy, created on Mar. 29, 2016, is named 126036-04902_SL.txt and is 34,331 bytes in size.

TECHNICAL FIELD

The present disclosure provides compositions and methods relating to or derived from anti-CD47 antibodies. More specifically, the present disclosure provides fully human antibodies that bind CD47, CD47-antibody binding fragments and derivatives of such antibodies, and CD47-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating a disease.

BACKGROUND

CD47, also known as integrin-associated protein (IAP), ovarian cancer antigen OA3, Rh-related antigen and MER6, is a multi-spanning transmembrane receptor belonging to the immunoglobulin superfamily CD47 expression and/or activity have been implicated in a number of diseases and disorders. Accordingly, there exists a need for therapies that target CD47. These and other deficiencies in the previous antibodies are overcome by the provision of fully human antibodies to CD47 by the present disclosure.

SUMMARY OF THE INVENTION

In certain embodiments, the present disclosure provides a fully human antibody of an IgG class that binds to a CD47 epitope with a binding affinity of at least $10^{-6}$M, which has a heavy chain variable domain sequence that is at least 95% identical to the amino acid sequences selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO: 22, SEQ ID NO: 24, and SEQ ID NO: 32, and combinations thereof, and that has a light chain variable domain sequence that is at least 95% identical to the amino acid sequence consisting of SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO: 23, SEQ ID NO: 25, SEQ ID NO: 26, SEQ ID NO: 27, SEQ ID NO: 28, SEQ ID NO: 29, and SEQ ID NO: 30, and combinations thereof. In one embodiment, the fully human antibody has both a heavy chain and a light chain wherein the antibody has a heavy chain/light chain variable domain sequence selected from the group consisting of SEQ ID NO. 1/SEQ ID NO. 2 (called C47A8 herein), SEQ ID NO. 1/SEQ ID NO. 4 (called C47B10 herein), SEQ ID NO. 1/SEQ ID NO. 5 (called C47B10-1H4S herein), SEQ ID NO. 1/SEQ ID NO. 6 (called C47B10-1F6S herein), SEQ ID NO:1/SEQ ID NO:8 (called C47B10-1 herein), SEQ ID NO. 7/SEQ ID NO. 8 (called C47B10-2A9S herein), SEQ ID NO. 9/SEQ ID NO. 8 (called C47B10-2B11S herein), SEQ ID NO. 10/SEQ ID NO. 4 (called C47B10-2B8S herein), SEQ ID NO. 11/SEQ ID NO. 4 (called C47B10-2C1S herein), SEQ ID NO. 12/SEQ ID NO. 4 (called C47B10-2B9S herein), SEQ ID NO. 13/SEQ ID NO. 4 (called 2C4S herein), SEQ ID NO. 14/SEQ ID NO. 15 (called C47B10-B1C herein), SEQ ID NO. 16/SEQ ID NO. 15 (called C47B10-C6C herein), SEQ ID NO. 17/SEQ ID NO. 15 (called C47B10-C3C herein), SEQ ID NO. 18/SEQ ID NO. 15 (called C47B10-D3C herein), SEQ ID NO. 19/SEQ ID NO. 15 (called C47B10-C11C herein), SEQ ID NO. 1/SEQ ID NO. 20 (called C47KD8 herein), SEQ ID NO. 1/SEQ ID NO. 21 (called C47KD9 herein), SEQ ID NO:1/SEQ ID NO:8 (C47B10-1H4S2), SEQ ID NO. 32/SEQ ID NO. 15 (C47B10-C3C), SEQ ID NO. 1/SEQ ID NO. 19 (C47K11), SEQ ID NO:22/SEQ ID NO:8 (C47B10-H3-D4), SEQ ID NO:1/SEQ ID NO:23 (C47B10-L1A-A10), SEQ ID NO:24/SEQ ID NO:8 (C47B10-H3-D3), SEQ ID NO:1/SEQ ID NO:25 (C47B10-L1A-A4), SEQ ID NO:1/SEQ ID NO:26 (C47B10-L3-B2), SEQ ID NO:1/SEQ ID NO:27 (C47A8-CA), SEQ ID NO:1/SEQ ID NO:28 (C47A8-CL), SEQ ID NO:1/SEQ ID NO:29 (C47-A8-CQ), and SEQ ID NO:1/SEQ ID NO:30 (C47A8-CS), and combinations thereof.

The present disclosure provides, in one embodiment, a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO: 22, SEQ ID NO: 24, and SEQ ID NO: 32, and combinations thereof, and that has a light chain variable domain sequence that is at least 95% identical to the amino acid sequence consisting of SEQ ID NO. 2, SEQ ID NO. 4, SEQ ID NO. 5, SEQ ID NO. 6, SEQ ID NO. 8, SEQ ID NO. 15, SEQ ID: 19, SEQ ID NO. 20, SEQ ID NO. 21, SEQ ID NO: 23, SEQ ID NO: 25, SEQ ID NO: 26, SEQ ID NO: 27, SEQ ID NO: 28, SEQ ID NO: 29, and SEQ ID NO: 30, and combinations thereof.

In one embodiment, the fully human antibody Fab fragment has both a heavy chain variable domain region and a light chain variable domain region wherein the antibody has a heavy chain/light chain variable domain sequence selected from the group consisting SEQ ID NO. 1/SEQ ID NO. 2, SEQ ID NO. 1/SEQ ID NO. 4, SEQ ID NO. 1/SEQ ID NO. 5, SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO. 14/SEQ ID NO. 15, SEQ ID NO. 16/SEQ ID NO. 15, SEQ ID NO. 17/SEQ ID NO. 15, SEQ ID NO. 18/SEQ ID NO. 15, SEQ ID NO. 19/SEQ ID NO. 15, SEQ ID NO. 1/SEQ ID NO. 20, SEQ ID NO. 1/SEQ ID NO. 21, SEQ ID NO:1/SEQ ID NO:8, SEQ ID NO. 32/SEQ ID NO. 15, SEQ ID NO. 1/SEQ ID NO. 19, SEQ ID NO:22/SEQ ID NO:8, SEQ ID NO:1/SEQ ID NO:23, SEQ ID NO:24/SEQ ID NO:8, SEQ ID NO:1/SEQ ID NO:25, SEQ ID NO:1/SEQ ID NO:26, SEQ ID NO:1/SEQ ID NO:27, SEQ ID NO:1/ SEQ ID NO:28, SEQ ID NO:1/SEQ ID NO:29, and SEQ ID NO:1/SEQ ID NO:30, and combinations thereof.

The present disclosure provides, in one embodiment, a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO: 22, SEQ ID NO: 24, and SEQ ID NO: 32, and that has a light chain variable domain sequence that is at least 95% identical to the amino acid sequence consisting of SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO: 23, SEQ ID NO: 25, SEQ ID NO: 26, SEQ ID NO: 27, SEQ ID NO: 28, SEQ ID NO: 29, and SEQ ID NO: 30, and combinations thereof. In one embodiment, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 1/SEQ ID NO. 4, SEQ ID NO. 1/SEQ ID NO. 5, SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO. 14/SEQ ID NO. 15, SEQ ID NO. 16/SEQ ID NO. 15, SEQ ID NO. 17/SEQ ID NO. 15, SEQ ID NO. 18/SEQ ID NO. 15, SEQ ID NO. 19/SEQ ID NO. 15, SEQ ID NO. 1/SEQ ID NO. 20, SEQ ID NO. 1/SEQ ID NO. 21, SEQ ID NO:1/SEQ ID NO:8, SEQ ID NO. 32/SEQ ID NO. 15, SEQ ID NO. 1/SEQ ID NO. 19, SEQ ID NO:22/SEQ ID NO:8, SEQ ID NO:1/SEQ ID NO:23, SEQ ID NO:24/SEQ ID NO:8, SEQ ID NO:1/SEQ ID NO:25, SEQ ID NO:1/SEQ ID NO:26, SEQ ID NO:1/SEQ ID NO:27, SEQ ID NO:1/ SEQ ID NO:28, SEQ ID NO:1/SEQ ID NO:29, and SEQ ID NO:1/SEQ ID NO:30, and combinations thereof.

The present disclosure further provides a method for treating a broad spectrum of mammalian cancers or a broad spectrum of fibrotic diseases, requiring either stimulation of immune responses or suppression, comprising administering an anti-CD47 polypeptide, wherein the fully human antibody has a heavy chain variable domain sequence that is at least 95% identical to the amino acid sequences selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO: 22, SEQ ID NO: 24, and SEQ ID NO: 32, and combinations thereof, and that has a light chain variable domain sequence that is at least 95% identical to the amino acid consisting of SEQ ID NO. 2, SEQ ID NO. 4, SEQ ID NO. 5, SEQ ID NO. 6, SEQ ID NO. 8, SEQ ID NO. 15, SEQ ID: 19, SEQ ID NO. 20, SEQ ID NO. 21, SEQ ID NO: 23, SEQ ID NO: 25, SEQ ID NO: 26, SEQ ID NO: 27, SEQ ID NO: 28, SEQ ID NO: 29, and SEQ ID NO: 30, combinations thereof. In one embodiment, the Fab fully human antibody fragment has the heavy chain variable domain sequence that is at least 95% identical to the amino acid sequences selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO: 22, SEQ ID NO: 24, and SEQ ID NO: 32, and combinations thereof, and that has the light chain variable domain sequence that is at least 95% identical to the amino acid sequence consisting of SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO: 23, SEQ ID NO: 25, SEQ ID NO: 26, SEQ ID NO: 27, SEQ ID NO: 28, SEQ ID NO: 29, and SEQ ID NO: 30, and combinations thereof. In one embodiment, the single chain human antibody has the heavy chain variable domain sequence that is at least 95% identical to the amino acid sequences selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO: 22, SEQ ID NO: 24, and SEQ ID NO: 32, and combinations thereof, and that has the light chain variable domain sequence that is at least 95% identical to the amino acid sequence consisting of SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO: 23, SEQ ID NO: 25, SEQ ID NO: 26, SEQ ID NO: 27, SEQ ID NO: 28, SEQ ID NO: 29, and SEQ ID NO: 30, and combinations thereof.

In one embodiment, the fully human antibody has both a heavy chain and a light chain wherein the antibody has a heavy chain/light chain variable domain sequence selected from the group consisting of SEQ ID NO. 1/SEQ ID NO. 2 (called C47A8 herein), SEQ ID NO. 1/SEQ ID NO. 4 (called C47B10 herein), SEQ ID NO. 1/SEQ ID NO. 5 (called C47B10-1H4S herein), SEQ ID NO. 1/SEQ ID NO. 6 (called C47B10-1F6S herein), SEQ ID NO. 7/SEQ ID NO. 8 (called C47B10-2A9S herein), SEQ ID NO. 9/SEQ ID NO. 8 (called C47B10-2B11S herein), SEQ ID NO. 10/SEQ ID NO. 4 (called C47B10-2B8S herein), SEQ ID NO. 11/SEQ ID NO. 4 (called C47B10-2C1S herein), SEQ ID NO. 12/SEQ ID NO. 4 (called C47B10-2B9S herein), SEQ ID NO. 13/SEQ ID NO. 4 (called 2C4S herein), SEQ ID NO. 14/SEQ ID NO. 15 (called C47B10-B1C herein), SEQ ID NO. 16/SEQ ID NO. 15 (called C47B10-C6C herein), SEQ ID NO. 17/SEQ ID NO. 15 (called C47B10-C3C herein), SEQ ID NO. 18/SEQ ID NO. 15 (called C47B10-D3C herein), SEQ ID NO. 19/SEQ ID NO. (called C47B10-C11C herein), SEQ ID NO. 1/SEQ ID NO. 20 (called C47KD8 herein), SEQ ID NO. 1/SEQ ID NO. 21 (called C47KD9 herein), SEQ ID NO:1/SEQ ID NO:8 (C47B10-1H4S2), SEQ ID NO. 32/SEQ ID NO. 15 (C47B10-C3C), SEQ ID NO. 1/SEQ ID NO. 19 (C47K11), SEQ ID NO:22/ SEQ ID NO:8 (C47B10-H3-D4), SEQ ID NO:1/SEQ ID NO:23 (C47B10-L1A-A10), SEQ ID NO:24/SEQ ID NO:8 (C47B10-H3-D3), SEQ ID NO:1/SEQ ID NO:25 (C47B10-L1A-A4), SEQ ID NO:1/SEQ ID NO:26 (C47B10-L3-B2), SEQ ID NO:1/SEQ ID NO:27 (C47A8-CA), SEQ ID NO:1/ SEQ ID NO:28 (C47A8-CL), SEQ ID NO:1/SEQ ID NO:29 (C47-A8-CQ), and SEQ ID NO:1/SEQ ID NO:30 (C47A8-CS), and combinations thereof. In one embodiment, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 1/SEQ ID NO. 4, SEQ ID NO. 1/SEQ ID NO. 5, SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO.

14/SEQ ID NO. 15, SEQ ID NO. 16/SEQ ID NO. 15, SEQ ID NO. 17/SEQ ID NO. 15, SEQ ID NO. 18/SEQ ID NO. 15, SEQ ID NO. 19/SEQ ID NO. 15, SEQ ID NO. 1/SEQ ID NO. 20, SEQ ID NO. 1/SEQ ID NO. 21, SEQ ID NO:1/SEQ ID NO:8, SEQ ID NO. 32/SEQ ID NO. 15, SEQ ID NO. 1/SEQ ID NO. 19, SEQ ID NO:22/SEQ ID NO:8, SEQ ID NO:1/SEQ ID NO:23, SEQ ID NO:24/SEQ ID NO:8, SEQ ID NO:1/SEQ ID NO:25, SEQ ID NO:1/SEQ ID NO:26, SEQ ID NO:1/SEQ ID NO:27, SEQ ID NO:1/SEQ ID NO:28, SEQ ID NO:1/SEQ ID NO:29, and SEQ ID NO:1/SEQ ID NO:30, and combinations thereof.

In one embodiment, the broad spectrum of mammalian cancers to be treated is selected from the group consisting of ovarian, colon, breast, lung cancers, myelomas, neuroblastic-derived CNS tumors, monocytic leukemias, B-cell derived leukemias, T-cell derived leukemias, B-cell derived lymphomas, T-cell derived lymphomas, mast cell derived tumors, and combinations thereof.

In one embodiment, the broad spectrum of fibrotic diseases to be treated is selected from the group consisting of myocardial infarction, angina, osteoarthritis, pulmonary fibrosis, asthma, cystic fibrosis, bronchitis, asthma, and combinations thereof.

This invention pertains to binding proteins capable of binding to CD47, including anti-CD47 antibodies, and antigen-binding fragments thereof.

In one aspect, the present disclosure provides an isolated fully human anti-CD47 antibody of an IgG class that binds to a CD47 epitope with a binding affinity of at least $10^{-6}$M, which has a heavy chain variable domain sequence that is at least 95% identical to the amino acid sequences selected from the group consisting of SEQ ID NO: 1, SEQ ID NO. 7, SEQ ID NO: 9, SEQ ID NO: 10, SEQ ID NO: 11, SEQ ID NO: 12, SEQ ID NO: 13, SEQ ID NO: 14, SEQ ID NO: 16, SEQ ID NO: 17, SEQ ID NO: 18, SEQ ID NO: 22, SEQ ID NO: 24, and SEQ ID NO: 32, and a light chain variable domain sequence that is at least 95% identical to the amino acid sequence selected from the group consisting of SEQ ID NO: 2, SEQ ID NO: 4, SEQ ID NO: 5, SEQ ID NO: 6, SEQ ID NO: 8, SEQ ID NO: 15, SEQ ID NO: 19, SEQ ID NO: 20, SEQ ID NO: 21, SEQ ID NO: 23, SEQ ID NO: 25, SEQ ID NO: 26, SEQ ID NO: 27, SEQ ID NO: 28, SEQ ID NO: 29, and SEQ ID NO: 30. In one embodiment, the fully human antibody has both a heavy chain and a light wherein the antibody has a heavy chain/light chain variable domain sequence selected from the group consisting of SEQ ID NO. 1/SEQ ID NO. 2 (C47A8), SEQ ID NO. 1/SEQ ID NO. 4 (C47B10), SEQ ID NO. 1/SEQ ID NO. 5 (C47B10-1H4S), SEQ ID NO:1/SEQ ID NO:8 (C47B10-1), SEQ ID NO. 1/SEQ ID NO. 6 (C47B10-1F6S), SEQ ID NO. 7/SEQ ID NO. 8 (C47B10-2A9S), SEQ ID NO. 9/SEQ ID NO. 8 (C47B10-2B11S), SEQ ID NO. 10/SEQ ID NO. 4 (C47B10-2B8S), SEQ ID NO. 11/SEQ ID NO. 4 (C47B10-2C1S), SEQ ID NO. 12/SEQ ID NO. 4 (C47B10-2B9S), SEQ ID NO. 13/SEQ ID NO. 4 (2C4S), SEQ ID NO. 14/SEQ ID NO. 15 (C47B10-B1C), SEQ ID NO. 16/SEQ ID NO. 15 (C47B10-C6C herein), SEQ ID NO. 17/SEQ ID NO. 15 (C47B10-D3C), SEQ ID NO. 18/SEQ ID NO. 15 (C47B10-C11C), SEQ ID NO. 19/SEQ ID NO. 15 (C47B10-C11C), SEQ ID NO. 1/SEQ ID NO. 20 (C47KD8), SEQ ID NO. 1/SEQ ID NO. 21 (C47KD9), SEQ ID NO:1/SEQ ID NO:8 (C47B10-1H4S2), SEQ ID NO. 32/SEQ ID NO. 15 (C47B10-C3C), SEQ ID NO. 1/SEQ ID NO. 19 (C47K11), SEQ ID NO:22/SEQ ID NO:8 (C47B10-H3-D4), SEQ ID NO:1/SEQ ID NO:23 (C47B10-L1A-A10), SEQ ID NO:24/SEQ ID NO:8 (C47B10-H3-D3), SEQ ID NO:1/SEQ ID NO:25 (C47B10-L1A-A4), SEQ ID NO:1/SEQ ID NO:26 (C47B10-L3-B2), SEQ ID NO:1/SEQ ID NO:27 (C47A8-CA), SEQ ID NO:1/SEQ ID NO:28 (C47A8-CL), SEQ ID NO:1/SEQ ID NO:29 (C47-A8-CQ), and SEQ ID NO:1/SEQ ID NO:30 (C47A8-CS).

In another aspect, the present invention provides an anti-CD47 Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO: 1, SEQ ID NO. 7, SEQ ID NO: 9, SEQ ID NO: 10, SEQ ID NO: 11, SEQ ID NO: 12, SEQ ID NO: 13, SEQ ID NO: 14, SEQ ID NO: 16, SEQ ID NO: 17, SEQ ID NO: 18, SEQ ID NO: 22, SEQ ID NO: 24, and SEQ ID NO: 32, and that has a light chain variable domain sequence that is at least 95% identical to the amino acid sequence consisting of SEQ ID NO: 2, SEQ ID NO: 4, SEQ ID NO: 5, SEQ ID NO: 6, SEQ ID NO: 8, SEQ ID NO: 15, SEQ ID NO: 19, SEQ ID NO: 20, SEQ ID NO: 21, SEQ ID NO: 23, SEQ ID NO: 25, SEQ ID NO: 26, SEQ ID NO: 27, SEQ ID NO: 28, SEQ ID NO: 29, and SEQ ID NO: 30. In one embodiment, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 1/SEQ ID NO. 4, SEQ ID NO. 1/SEQ ID NO. 5, SEQ ID NO:1/SEQ ID NO:8, SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO. 14/SEQ ID NO. 15, SEQ ID NO. 16/SEQ ID NO. 15, SEQ ID NO. 17/SEQ ID NO. 15, SEQ ID NO. 18/SEQ ID NO. 15, SEQ ID NO. 1/SEQ ID NO. 20, SEQ ID NO. 1/SEQ ID NO. 21, SEQ ID NO. 1/SEQ ID NO. 22, SEQ ID NO:1/SEQ ID NO:8, SEQ ID NO. 32/SEQ ID NO. 15, SEQ ID NO. 1/SEQ ID NO. 19, SEQ ID NO:22/SEQ ID NO:8, SEQ ID NO:1/SEQ ID NO:23, SEQ ID NO:24/SEQ ID NO:8, SEQ ID NO:1/SEQ ID NO:25, SEQ ID NO:1/SEQ ID NO:26, SEQ ID NO:1/SEQ ID NO:27, SEQ ID NO:1/SEQ ID NO:28, SEQ ID NO:1/SEQ ID NO:29, and SEQ ID NO:1/SEQ ID NO:30.

In another aspect, the present disclosure provides an anti-CD47 single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO: 22, SEQ ID NO: 24, and SEQ ID NO: 32, and that has a light chain variable domain sequence that is at least 95% identical to the amino acid sequence consisting of SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO: 23, SEQ ID NO: 25, SEQ ID NO: 26, SEQ ID NO: 27, SEQ ID NO: 28, SEQ ID NO: 29, and SEQ ID NO: 30.

In one embodiment, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 1/SEQ ID NO. 4, SEQ ID NO. 1/SEQ ID NO. 5, SEQ ID NO:1/SEQ ID NO:8 (C47B10-1), SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO. 14/SEQ ID NO. 15, SEQ ID NO. 16/SEQ ID NO. 15, SEQ ID NO. 17/SEQ ID NO. 15, SEQ ID NO. 18/SEQ ID NO. 15, SEQ ID NO. 19/SEQ ID NO. 15, SEQ ID NO. 1/SEQ ID NO. 20, SEQ ID NO. 1/SEQ ID NO. 21, SEQ ID NO. 1/SEQ ID NO. 22, SEQ ID NO:1/SEQ ID NO:8, SEQ ID NO. 32/SEQ ID NO. 15, SEQ ID NO. 1/SEQ ID NO. 19, SEQ ID NO:22/SEQ ID NO:8, SEQ ID NO:1/SEQ ID NO:23, SEQ ID NO:24/SEQ ID NO:8, SEQ ID NO:1/SEQ ID NO:25, SEQ ID NO:1/SEQ ID NO:26, SEQ ID NO:1/SEQ ID NO:27, SEQ ID NO:1/SEQ ID NO:28, SEQ ID NO:1/SEQ ID NO:29, and SEQ ID NO:1/SEQ ID NO:30.

Also included in the invention, is an isolated anti-CD47 antibody, or antigen-binding fragment thereof, comprising a heavy chain variable domain comprising complementarity determining regions (CDRs) as set forth in a heavy chain variable region amino acid sequence selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO: 22, SEQ ID NO: 24, and SEQ ID NO: 32, and comprising a light chain variable region comprising CDRs as set forth in a light chain variable region amino acid sequence selected from the group consisting of SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO: 23, SEQ ID NO: 25, SEQ ID NO: 26, SEQ ID NO: 27, SEQ ID NO: 28, SEQ ID NO: 29, and SEQ ID NO: 30.

The present disclosure further provides a method for treating a cancer or a fibrotic disease, said method comprising administering an anti-CD47 polypeptide, wherein the anti-CD47 polypeptide is selected form the group consisting of an isolated fully human antibody of an IgG class that binds to CD47 and comprises a heavy chain variable domain and a light chain variable domain; an anti-CD47 fully human antibody Fab fragment comprising a heavy chain variable domain and a light chain variable domain; and a single chain human antibody comprising a heavy chain variable domain and a light chain variable domain, wherein the heavy chain variable domain and the light chain variable domain are connected via a peptide linker; wherein the heavy chain variable domain comprises an amino acid sequence that is at least 95% identical to an amino acid sequence selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO: 22, SEQ ID NO: 24, and SEQ ID NO: 32, and that has a light chain variable domain sequence that is at least 95% identical to the amino acid sequence selected from the group consisting of SEQ ID NO. 2, SEQ ID NO. 4, SEQ ID NO. 5, SEQ ID NO. 6, SEQ ID NO. 8, SEQ ID NO. 15, SEQ ID NO. 19, SEQ ID NO. 20, SEQ ID NO. 21, SEQ ID NO: 23, SEQ ID NO: 25, SEQ ID NO: 26, SEQ ID NO: 27, SEQ ID NO: 28, SEQ ID NO: 29, and SEQ ID NO: 30.

In certain embodiments, the fully human antibody or antibody fragment has both a heavy chain and a light chain wherein the antibody or antibody fragment comprises a heavy chain/light chain variable domain sequence selected from the group consisting of SEQ ID NO. 1/SEQ ID NO. 2, SEQ ID NO. 1/SEQ ID NO. 4, SEQ ID NO. 1/SEQ ID NO. 5, SEQ ID NO:1/SEQ ID NO:8 (C47B10-1), SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO. 14/SEQ ID NO. 15, SEQ ID NO. 16/SEQ ID NO. 15, SEQ ID NO. 17/SEQ ID NO. 15, SEQ ID NO. 18/SEQ ID NO. 15, SEQ ID NO. 19/SEQ ID NO. 15, SEQ ID NO. 1/SEQ ID NO. 20, SEQ ID NO. 1/SEQ ID NO. 21, SEQ ID NO. 1/SEQ ID NO. 22, SEQ ID NO:1/SEQ ID NO:8, SEQ ID NO. 32/SEQ ID NO. 15, SEQ ID NO. 1/SEQ ID NO. 19, SEQ ID NO:22/SEQ ID NO:8, SEQ ID NO:1/SEQ ID NO:23, SEQ ID NO:24/SEQ ID NO:8, SEQ ID NO:1/SEQ ID NO:25, SEQ ID NO:1/SEQ ID NO:26, SEQ ID NO:1/SEQ ID NO:27, SEQ ID NO:1/SEQ ID NO:28, SEQ ID NO:1/SEQ ID NO:29, and SEQ ID NO:1/SEQ ID NO:30.

In certain embodiments, the antibody, or antigen-binding fragment thereof, of the invention has a $K_D$ of at least $1\times10^{-6}$ M. In other embodiments, the antibody, or antigen-binding fragment thereof, of the invention has a $K_D$ of at least $1\times10^{-7}$ M. In other embodiments, the antibody, or antigen-binding fragment thereof, of the invention has a $K_D$ of at least $1\times10^{-8}$ M.

In certain embodiments, the antibody is an IgG1 isotype. In other embodiments, the antibody is an IgG4 isotype.

In certain embodiments, the anti-CD47 antibody, or antigen-binding fragment, described herein is recombinant. In certain embodiments, the anti-CD47 antibody, or antigen-binding fragment, described herein is a human antibody, or antigen-binding fragment.

The invention also provides pharmaceutical compositions comprising an effective amount of an anti-CD47 antibodies or fragments disclosed herein, and a pharmaceutically acceptable carrier.

In certain embodiments, the invention features a method of treating cancer or a fibrotic disease in a human subject in need thereof, comprising administering an effective amount of an anti-CD47 antibody, or antigen-binding fragment thereof, disclosed herein to the subject, such that cancer is treated.

In one embodiment, the cancer is selected from the group consisting of ovarian cancer, colon cancer, breast cancer, lung cancer, myelomas, neuroblastic-derived CNS tumors, monocytic leukemias, B-cell derived leukemias, T-cell derived leukemias, B-cell derived lymphomas, T-cell derived lymphomas, and mast cell derived tumors.

In another embodiment, the fibrotic disease is selected from the group consisting of myocardial infarction, angina, osteoarthritis, pulmonary fibrosis, asthma, cystic fibrosis, bronchitis, and asthma.

DETAILED DESCRIPTION

Definitions

Figure 1:
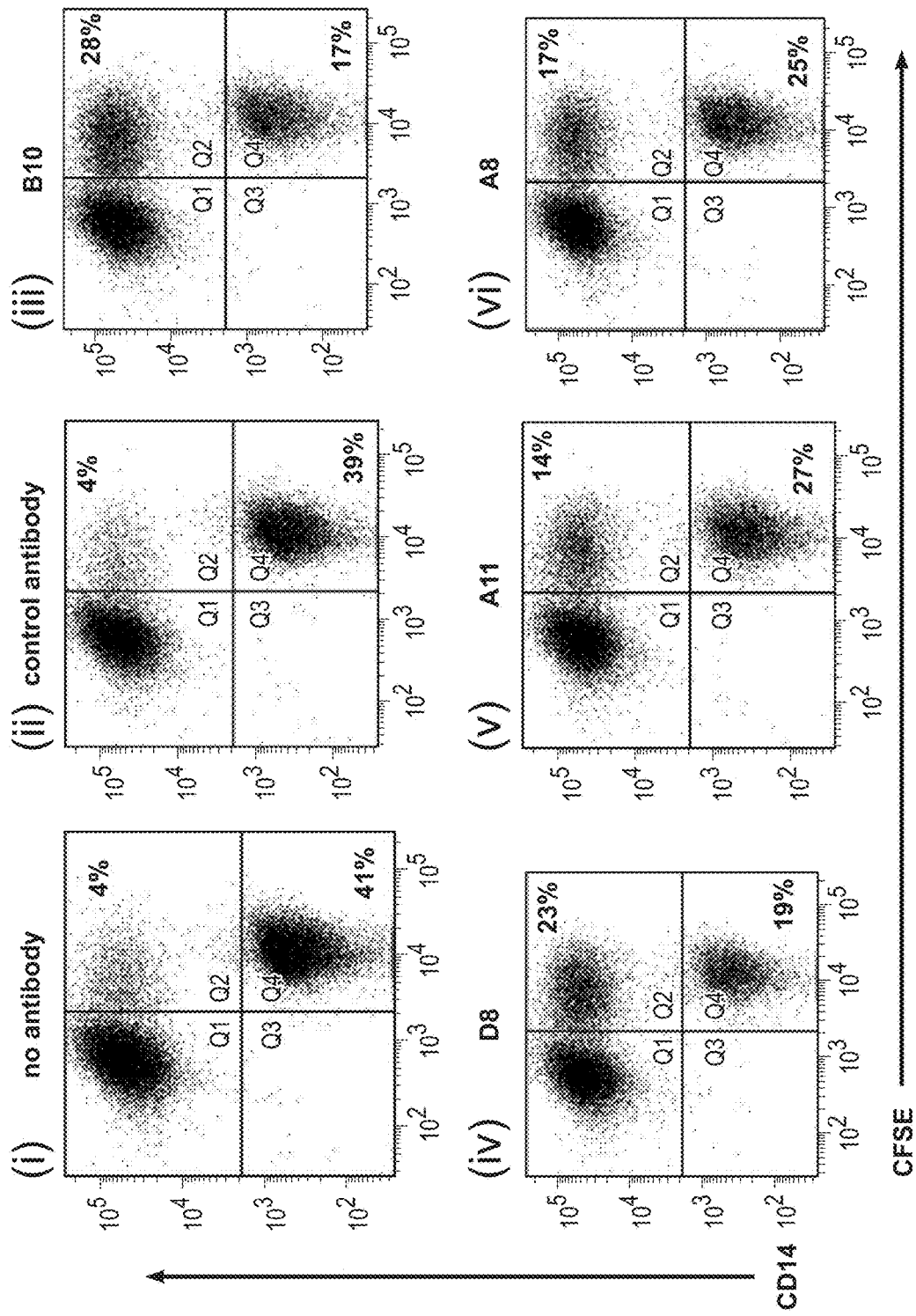
FIG. 1 demonstrates the ability of anti-CD47 antibodies, but not the control antibody, to promote the phagocytosis of K562. The results shown in FIG. 1 are from a flow cytometry assay. The cell populations in the upper right quadrant represent the macrophages with phaocytosed K562 cells. The cells in the lower right quadrant are the K562 cells which have not been phagocytosed. The panels in FIG. 1 represent the following: (i) no antibody; (ii) control antibody (an isotype matched negative control antibody (i.e., an antibody that not only does not bind CD47, but does not bind to the cells); (iii) B10; (iv) D8; (v) A11; (vi) A8. All the anti-CD47 antibodies tested exhibited some activity with B10 (iii) promoting the most phagocytosis.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, a variant of an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a confirmation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of an immunoglobulin. An "immunoglobulin" is a tetrameric molecule composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. In one embodiment, the anti-CD47 antibodies disclosed herein are characterized by their variable domain region sequences in the heavy $V_H$ and light $V_L$ amino acid sequences. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

The variable regions of immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5th Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, Dev. Comp. Immunol. 29:185-203; 2005) and AHo (Honegger and Pluckthun, J. Mol. Biol. 309(3):657-670; 2001).

An "antibody" refers to an intact immunoglobulin or to an antigen binding portion thereof that competes with the intact antibody for specific binding, unless otherwise specified. In one embodiment, an antibody comprises a heavy chain comprising a heavy chain variable domain and heavy chain constant regions $C_{H1}$, $C_{H2}$ and $C_{H3}$, and a light chain comprising a light chain variable domain a light chain constant region ($C_L$). The heavy and light chain variable domain sequences may be selected from those described herein in SEQ ID NOs: 1 to 32.

Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

In certain embodiments, antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific."

The term "monospecific", as used herein, refers to an antibody that displays an affinity for one particular epitope.

Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody fragment" or "antigen binding fragment of an antibody" comprises a portion of an intact antibody, and preferably comprises the antibody antigen binding or variable domains. Examples of an antibody fragment include a Fab, an Fab', an F(ab')2, an Fv fragment, and a linear antibody.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634; 6,696,245, US App. Pub. 20/0202512; 2004/0202995; 2004/0038291; 2004/0009507; 20 03/0039958, and Ward et al., *Nature* 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83).

Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

An antigen binding protein, such as an antibody, may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes antibodies that have one or more variable and constant regions derived from human immunoglobulin sequences. In one embodiment, all of the variable and constant domains of the antibody are derived from human immunoglobulin sequences (referred to as a "fully human antibody"). These antibodies may be prepared in a variety of ways, examples of which are described below, including through the immunization with an antigen of interest of a mouse that is genetically modified to express antibodies derived from human heavy and/or light chain-encoding genes. In a preferred embodiment, a fully human antibody is made using recombinant methods such that the glycosylation pattern of the antibody is different than an antibody having the same amino acid sequence if it were to exist in nature.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-CD47 antibody. In another embodiment, all of the CDRs are derived from a human anti-CD47 antibody. In another embodiment, the CDRs from more than one human anti-CD47 antibodies are mixed and matched in a chimeric antibody. For instance, a chimeric antibody may comprise a CDR1 from the light chain of a first human anti-CD47 antibody, a CDR2 and a CDR3 from the light chain of a second human anti-CD47 antibody, and the CDRs from the heavy chain from a third anti-CD47 antibody. Other combinations are possible.

Further, the framework regions may be derived from one of the same anti-CD47 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind CD47).

An "inhibitory antibody" is an antibody that inhibits the activity of CD47. In one embodiment, an anti-CD47 antibody is an inhibitory antibody if the antibody can prevent binding of CD47 with its ligand signal regulatory protein-α (SIRPα). In one embodiment, an anti-CD47 inhibitory antibody inhibits the proteolytic activation of CD47 when an excess of the anti-CD47 antibody reduces the amount of CD47 activation by at least about 20%. CD47 activation can be determined by any of various methods known in the art, for example using an assay such as those described herein in the Examples. In various embodiments, the antigen binding protein reduces the amount of amount of proteolytic activation of CD47 by at least 30%, 40%, 50%, 60%, 70%, 75%, 80%, 85%, 90%, 95%, 97%, 99%, and 99.9%.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human CD47) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "recombinant antibody" refers to an antibody that is expressed from a cell or cell line transfected with an expression vector (or possibly more than one expression vector) comprising the coding sequence of the antibody (or portion thereof), where said coding sequence is not naturally associated with the cell. In one embodiment, a recombinant antibody has a glycosylation pattern that is different than the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns.

The term "effective amount" as used herein, refers to that amount of an antibody, or an antigen binding portion thereof that binds CD47, which is sufficient to effect treatment, prognosis or diagnosis of a disease associated with CD47 dependent signaling, as described herein, when administered to a subject. Therapeutically effective amounts of antibodies provided herein, when used alone or in combination, will vary depending upon the relative activity of the antibodies (e.g., promoting macrophage mediated phagocytosis of cancer cells expressing CD47) and depending upon the subject and disease condition being treated, the weight and age of the subject, the severity of the disease condition, the manner of administration and the like, which can readily be determined by one of ordinary skill in the art.

The term "isolated", as used herein, refers a protein (e.g., an antibody) that is substantially free of other cellular material. In one embodiment, an isolated antibody is substantially free of other proteins from the same species. In one embodiment, an isolated antibody is expressed by a cell from a different species and is substantially free of other proteins from the different species. A protein may be rendered substantially free of naturally associated components (or components associated with the cellular expression system used to produce the antibody) by isolation, using protein purification techniques well known in the art. In one embodiment, the antibodies, or antigen binding fragments, of the invention are isolated.

CD47 Antigen Binding Proteins

The present invention pertains to CD47 binding proteins, particularly anti-CD47 antibodies, or antigen-binding portions thereof, that bind to CD47, e.g., human CD47, and uses thereof. Various aspects of the invention relate to antibodies and antibody fragments, pharmaceutical compositions, nucleic acids, recombinant expression vectors, and host cells for making such antibodies and fragments. Methods of using the antibodies of the invention to detect human CD47, to inhibit CD47 activity, either in vitro or in vivo, and to prevent or treat disorders such as cancer are also encompassed by the invention.

As described in Table 5 below, included in the invention are novel antibody heavy and light chain variable regions that are specific to CD47. In one embodiment, the invention provides an anti-CD47 antibody, or an antigen-binding fragment thereof, that comprises a heavy chain having a variable domain comprising an amino acid sequence as set forth in any one of SEQ ID Nos: 1, 7, 9, 10, 11, 12, 13, 14, 16, 17, 18, 22, 24 and 32. In one embodiment, the invention provides an anti-CD47 antibody, or an antigen-binding fragment thereof, that comprises a light chain having a variable domain comprising an amino acid sequence as set forth in any one of SEQ ID Nos: 2, 4, 5, 6, 8, 15, 19, 20, 21, 23, 25, 26, 27, 28, 29, and 30. In one embodiment, the invention provides an anti-CD47 antibody, or an antigen-binding fragment thereof, that comprises a light chain having a variable domain comprising an amino acid sequence as set forth in any one of SEQ ID Nos: 2, 4, 5, 6, 8, 15, 19, 20, 21, 23, 25, 26, 27, 28, 29 and 30; and a heavy chain having a variable domain comprising an amino acid sequence as set forth in any one of SEQ ID Nos: 1, 7, 9, 10, 11, 12, 13, 14, 16, 17, 18, 22, 24 and 32.

Complementarity determining regions (CDRs) are known as hypervariable regions both in the light chain and the heavy chain variable domains. The more highly conserved portions of variable domains are called the framework (FR). Complementarity determining regions (CDRs) and framework regions (FR) of a given antibody may be identified using the system described by Kabat et al. supra; Lefranc et al., supra and/or Honegger and Pluckthun, supra. Also familiar to those in the art is the numbering system described in Kabat et al. (1991, NIH Publication 91-3242, National Technical Information Service, Springfield, Va.). In this regard Kabat et al. defined a numbering system for variable domain sequences that is applicable to any antibody. One of ordinary skill in the art can unambiguously assign this system of "Kabat numbering" to any variable domain amino acid sequence, without reliance on any experimental data beyond the sequence itself.

In certain embodiments, the present invention provides an anti-CD47 antibody comprising the CDRs of a heavy and a light chain variable domain as described in Table 5 (SEQ ID Nos: 1 to 32). For example, the invention provides an anti-CD47 antibody, or antigen-binding fragment thereof, comprising a heavy chain variable region having the CDRs described in an amino acid sequence as set forth in any one of SEQ ID Nos: 1, 7, 9, 10, 11, 12, 13, 14, 16, 17, 18, 22, 24 and 32. In one embodiment, the invention provides an anti-CD47 antibody, or antigen-binding fragment thereof, comprising a light chain variable region having the CDRs described in an amino acid sequence as set forth in any one of SEQ ID Nos: 2, 4, 5, 6, 8, 15, 19, 20, 21, 23, 25, 26, 27, 28, 29 and 30. In one embodiment, the invention provides an anti-CD47 antibody, or antigen-binding fragment thereof, comprising a light chain variable region having the CDRs described in an amino acid sequence as set forth in any one of SEQ ID Nos: 2, 4, 5, 6, 8, 15, 19, 20, 21, 23, 25, 26, 27, 28, 29 and 30; and a heavy chain variable region having the CDRs described in an amino acid sequence as set forth in any one of SEQ ID Nos: 1, 7, 9, 10, 11, 12, 13, 14, 16, 17, 18, 22, 24 and 32.

One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

In one embodiment, the present disclosure provides a fully human antibody of an IgG class that binds to a CD47 epitope and has a heavy chain variable domain sequence that is at least 95% identical, at least 96% identical, at least 97% identical, at least 98% identical, or at least 99% identical to an amino acid sequence selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, 22, SEQ ID NO: 24, SEQ ID NO:32, and combinations thereof, and has a light chain variable domain sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO. 23, SEQ ID NO: 25, SEQ ID NO: 26, SEQ ID NO: 27, SEQ ID NO: 28, SEQ ID NO: 29, and SEQ ID NO: 30, and combinations thereof. In one embodiment, the antibody of an IgG class that binds to CD47 has a binding affinity for CD47 of $10^{-6}$M or less. In one embodiment, the fully human antibody has both a heavy chain and a light chain wherein the antibody has a heavy chain/light chain variable domain sequence selected from the group consisting of SEQ ID NO. 1/SEQ ID NO. 2 (called C47A8 herein), SEQ ID NO. 1/SEQ ID NO. 4 (called C47B10 herein), SEQ ID NO. 1/SEQ ID NO. 5 (called C47B10-1H4S herein), SEQ ID NO:1/SEQ ID NO:8 (called C47B10-1 herein), SEQ ID NO. 1/SEQ ID NO. 6 (called C47B10-1F6S herein), SEQ ID NO. 7/SEQ ID NO. 8 (called C47B10-2A9S herein), SEQ ID NO. 9/SEQ ID NO. 8 (called C47B10-2B11S herein), SEQ ID NO. 10/SEQ ID NO. 4 (called C47B10-2B8S herein), SEQ ID NO. 11/SEQ ID NO. 4 (called C47B10-2C1S herein), SEQ ID NO. 12/SEQ ID NO. 4 (called C47B10-2B9S herein), SEQ ID NO. 13/SEQ ID NO. 4 (called C47B10-2C4S herein), SEQ ID NO. 14/SEQ ID NO. 15 (called C47B10-B1C herein), SEQ ID NO. 16/SEQ ID NO. 15 (called C47B10-C6C herein), SEQ ID NO. 32/SEQ ID NO. 15 (called C47B10-C3C herein), SEQ ID NO. 17/SEQ ID NO. 15 (called C47B10-D3C herein), SEQ ID NO. 18/SEQ ID NO. 15 (called C47B10-C11C herein), SEQ ID NO. 1/SEQ ID NO. 19 (called C47K11 herein), SEQ ID NO. 1/SEQ ID NO. 20 (called C47KD8 herein), SEQ ID NO. 1/SEQ ID NO. 21 (called C47KD9 herein), SEQ ID NO:22/SEQ ID NO:8 (called C47B10-H3-D4 herein), SEQ ID NO:1/SEQ ID NO:23 (called C47 B10-L1A-A10 herein), SEQ ID NO:24/SEQ ID NO:8 (called C47B10-H3-D3), SEQ ID NO:1/SEQ ID NO:25 (called C47B10-L1A-A4 herein), SEQ ID NO:1/SEQ ID NO:26 (called C47B10-L3-B2 herein), SEQ ID NO:1/SEQ ID NO:27 (called C47-A8-CA herein), SEQ ID NO:1/SEQ ID NO:28 (called C47-A8-CL herein), SEQ ID NO:1/SEQ ID NO:29 (called C47-A8-CQ herein), and SEQ ID NO:1/SEQ ID NO:30 (called C47A8-CS herein, and combinations thereof.

It should be noted that the anti-CD47 antibodies described throughout are referred to with or without "C47" preceding the name. For example, C47KD8 is referred to throughout interchangeably as C47KD8 and KD8.

In one embodiment, the invention provides an anti-CD47 antibody, or an antigen-binding fragment thereof, comprising a heavy chain comprising a CDR3 domain as set forth in any one of SEQ ID Nos: 1, 7, 9, 10, 11, 12, 13, 14, 16, 17, 18, 22, 24 and 32, and comprising a variable domain comprising an amino acid sequence that has at least 95%, at least 96%, at least 97%, at least 98%, or at least 99% identity to a sequence as set forth in any one of SEQ ID Nos: 1, 7, 9, 10, 11, 12, 13, 14, 16, 17, 18, 22, 24 and 32. In one embodiment, the invention provides an anti-CD47 antibody, or an antigen-binding fragment thereof, comprising a light chain comprising a CDR3 domain as set forth in any one of SEQ ID Nos: 2, 4, 5, 6, 8, 15, 19, 20, 21, 23, 25, 26, 27, 28, 29 and 30, and having a light chain variable domain comprising an amino acid sequence that has at least 95%, at least 96%, at least 97%, at least 98%, or at least 99% identical to a sequence as set forth in any one of SEQ ID Nos: 2, 4, 5, 6, 8, 15, 19, 20, 21, 23, 25, 26, 27, 28, 29 and 30. Thus, in certain embodiments, the CDR3 domain is held constant, while variability may be introduced into the remaining CDRs and/or framework regions of the heavy and/or light chains, while the antibody, or antigen binding fragment thereof, retains the ability to bind to CD47 and retains the functional characteristics, e.g., binding affinity, of the parent.

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

In one embodiment, the present invention is directed to an antibody, or an antigen binding fragment thereof, having the antigen binding regions of any of the antibodies described in Table 5.

In one embodiment, the present invention is directed to an antibody, or antigen-binding fragment thereof, having the antigen binding regions of antibody C47A8. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 2. In one embodiment, the invention is directed to an antibody having a heavy chain variable domain comprising the CDRs of SEQ ID NO: 1, and a light chain variable domain comprising the CDRs of SEQ ID NO: 2. In one embodiment, the invention features an isolated human antibody, or anti-gen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 1, and comprises a light chain variable region having an amino acid sequence that is at least 95% identical, at least 96% identical, at least 97% identical, at least 98% identical, or at least 99% identical to the sequence set forth in SEQ ID NO. 2. The antibody may further be an IgG1 or an IgG4 isotype.

In one embodiment, the present invention is directed to an antibody, or antigen-binding fragment thereof, having the antigen binding regions of antibody C47B10. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 4. In one embodiment, the invention is directed to an antibody having a heavy chain variable domain comprising the CDRs of SEQ ID NO: 1, and a light chain variable domain comprising the CDRs of SEQ ID NO: 4. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 1, and comprises a light chain variable region having an amino acid sequence that is at least 95% identical, at least 96% identical, at least 97% identical, at least 98% identical, or at least 99% identical to the sequence set forth in SEQ ID NO. 4. The antibody may further be an IgG1 or an IgG4 isotype.

In one embodiment, the present invention is directed to an antibody, or antigen-binding fragment thereof, having the antigen binding regions of antibody C47B10-1H4S. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 5. In one embodiment, the invention is directed to an antibody having a heavy chain variable domain comprising the CDRs of SEQ ID NO: 1, and a light chain variable domain comprising the CDRs of SEQ ID NO: 5. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 1, and comprises a light chain variable region having an amino acid sequence that is at least 95% identical, at least 96% identical, at least 97% identical, at least 98% identical, or at least 99% identical to the sequence set forth in SEQ ID NO. 5. The antibody may further be an IgG1 or an IgG4 isotype.

In one embodiment, the present invention is directed to an antibody, or antigen-binding fragment thereof, having the antigen binding regions of antibody C47B10-1. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 8. In one embodiment, the invention is directed to an antibody having a heavy chain variable domain comprising the CDRs of SEQ ID NO: 1, and a light chain variable domain comprising the CDRs of SEQ ID NO: 8. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 1, and comprises a light chain variable region having an amino acid sequence that is at least 95% identical, at least 96% identical, at least 97% identical, at least 98% identical, or at least 99% identical to the sequence set forth in SEQ ID NO. 8. The antibody may further be an IgG1 or an IgG4 isotype.

In one embodiment, the present invention is directed to an antibody, or antigen-binding fragment thereof, having the antigen binding regions of antibody C47B10-1F6S. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 6. In one embodiment, the invention is directed to an antibody having a heavy chain variable domain comprising the CDRs of SEQ ID NO: 1, and a light chain variable domain comprising the CDRs of SEQ ID NO: 6. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 1, and comprises a light chain variable region having an amino acid sequence that is at least 95% identical, at least 96% identical, at least 97% identical, at least 98% identical, or at least 99% identical to the sequence set forth in SEQ ID NO. 6. The antibody may further be an IgG1 or an IgG4 isotype.

In one embodiment, the present invention is directed to an antibody, or antigen-binding fragment thereof, having the antigen binding regions of antibody C47B10-2A9S. In one embodiment, the invention provides an antibody, or antigen-binding fragment thereof, comprising a heavy chain variable domain sequence as set forth in SEQ ID NO: 7, and a light chain variable domain sequence as set forth in SEQ ID NO: 8. In one embodiment, the invention is directed to an antibody having a heavy chain variable domain comprising the CDRs of SEQ ID NO: 7, and a light chain variable domain comprising the CDRs of SEQ ID NO: 8. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 7, and comprises a light chain variable region having an amino acid sequence that is at least 95% identical, at least 96% identical, at least 97% identical, at least 98% identical, or at least 99% identical to the sequence set forth in SEQ ID NO. 8. The antibody may further be an IgG1 or an IgG4 isotype.

In one embodiment, the present invention is directed to an antibody, or antigen-binding fragment thereof, having the antigen binding regions of antibody C47B10-2B11S. In one embodiment, the invention provides an antibody, or antigen-binding fragment thereof, comprising a heavy chain variable domain sequence as set forth in SEQ ID NO: 9, and a light chain variable domain sequence as set forth in SEQ ID NO: 8. In one embodiment, the invention is directed to an antibody having a heavy chain variable domain comprising the CDRs of SEQ ID NO: 9, and a light chain variable domain comprising the CDRs of SEQ ID NO: 8. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 9, and comprises a light chain variable region having an amino acid sequence that is at least 95% identical, at least 96% identical, at least 97% identical, at least 98% identical, or at least 99% identical to the sequence set forth in SEQ ID NO. 8. The antibody may further be an IgG1 or an IgG4 isotype.

In one embodiment, the present invention is directed to an antibody, or antigen-binding fragment thereof, having the antigen binding regions of antibody C47B10-2B8S. In one embodiment, the invention provides an antibody, or antigen-binding fragment thereof, comprising a heavy chain variable domain sequence as set forth in SEQ ID NO: 10, and a light chain variable domain sequence as set forth in SEQ ID NO: 4. In one embodiment, the invention is directed to an antibody having a heavy chain variable domain comprising the CDRs of SEQ ID NO: 10, and a light chain variable domain comprising the CDRs of SEQ ID NO: 4. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 10, and comprises a light chain variable region having an amino acid sequence that is at least 95% identical, at least 96% identical, at least 97% identical, at least 98% identical, or at least 99% identical to the sequence set forth in SEQ ID NO. 4. The antibody may further be an IgG1 or an IgG4 isotype.

In one embodiment, the present invention is directed to an antibody, or antigen-binding fragment thereof, having the antigen binding regions of antibody C47B10-2C1S. In one embodiment, the invention provides an antibody, or antigen-binding fragment thereof, comprising a heavy chain variable domain sequence as set forth in SEQ ID NO: 11, and a light chain variable domain sequence as set forth in SEQ ID NO: 4. In one embodiment, the invention is directed to an antibody having a heavy chain variable domain comprising the CDRs of SEQ ID NO: 11, and a light chain variable domain comprising the CDRs of SEQ ID NO: 4. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 11, and comprises a light chain variable region having an amino acid sequence that is at least 95% identical, at least 96% identical, at least 97% identical, at least 98% identical, or at least 99% identical to the sequence set forth in SEQ ID NO. 4. The antibody may further be an IgG1 or an IgG4 isotype.

In one embodiment, the present invention is directed to an antibody, or antigen-binding fragment thereof, having the antigen binding regions of antibody C47B10-2B9S. In one embodiment, the invention provides an antibody, or antigen-binding fragment thereof, comprising a heavy chain variable domain sequence as set forth in SEQ ID NO: 12, and a light chain variable domain sequence as set forth in SEQ ID NO: 4. In one embodiment, the invention is directed to an antibody having a heavy chain variable domain comprising the CDRs of SEQ ID NO: 12, and a light chain variable domain comprising the CDRs of SEQ ID NO: 4. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 12, and comprises a light chain variable region having an amino acid sequence that is at least 95% identical, at least 96% identical, at least 97% identical, at least 98% identical, or at least 99% identical to the sequence set forth in SEQ ID NO. 4. The antibody may further be an IgG1 or an IgG4 isotype.

In one embodiment, the present invention is directed to an antibody, or antigen-binding fragment thereof, having the antigen binding regions of antibody C47B10-2C4S. In one embodiment, the invention provides an antibody, or antigen-binding fragment thereof, comprising a heavy chain variable domain sequence as set forth in SEQ ID NO: 13, and a light chain variable domain sequence as set forth in SEQ ID NO: 4. In one embodiment, the invention is directed to an antibody having a heavy chain variable domain comprising the CDRs of SEQ ID NO: 13, and a light chain variable domain comprising the CDRs of SEQ ID NO: 4. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO. 13, and comprises a light chain variable region having an amino acid sequence that is at least 95% identical, at least 96% identical, at least 97% identical, at least 98% identical, or at least 99% identical to the sequence set forth in SEQ ID NO. 4. The antibody may further be an IgG1 or an IgG4 isotype.

In one embodiment, the present invention is directed to an antibody, or antigen-binding fragment thereof, having the antigen binding regions of antibody C47B10-B1C. In one embodiment, the invention provides an antibody, or antigen-binding fragment thereof, comprising a heavy chain variable domain sequence as set forth in SEQ ID NO: 14, and a light chain variable domain sequence as set forth in SEQ ID NO: 15. In one embodiment, the invention is directed to an antibody having a heavy chain variable domain comprising the CDRs of SEQ ID NO: 14, and a light chain variable domain comprising the CDRs of SEQ ID NO: 15. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 14, and comprises a light chain variable region having an amino acid sequence that is at least 95% identical, at least 96% identical, at least 97% identical, at least 98% identical, or at least 99% identical to the sequence set forth in SEQ ID NO: 15. The antibody may further be an IgG1 or an IgG4 isotype.

In one embodiment, the present invention is directed to an antibody, or antigen-binding fragment thereof, having the antigen binding regions of antibody C47B10-C6C. In one embodiment, the invention provides an antibody, or antigen-binding fragment thereof, comprising a heavy chain variable domain sequence as set forth in SEQ ID NO: 16, and a light chain variable domain sequence as set forth in SEQ ID NO: 15. In one embodiment, the invention is directed to an antibody having a heavy chain variable domain comprising the CDRs of SEQ ID NO: 16, and a light chain variable domain comprising the CDRs of SEQ ID NO: 15. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 16, and comprises a light chain variable region having an amino acid sequence that is at least 95% identical, at least 96% identical, at least 97% identical, at least 98% identical, or at least 99% identical to the sequence set forth in SEQ ID NO: 15. The antibody may further be an IgG1 or an IgG4 isotype.

In one embodiment, the present invention is directed to an antibody, or antigen-binding fragment thereof, having the antigen binding regions of antibody C47B10-C3C. In one embodiment, the invention provides an antibody, or antigen-binding fragment thereof, comprising a heavy chain variable domain sequence as set forth in SEQ ID NO: 32, and a light chain variable domain sequence as set forth in SEQ ID NO: 15. In one embodiment, the invention is directed to an antibody having a heavy chain variable domain comprising the CDRs of SEQ ID NO: 32, and a light chain variable domain comprising the CDRs of SEQ ID NO: 15. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 32, and comprises a light chain variable region having an amino acid sequence that is at least 95% identical, at least 96% identical, at least 97% identical, at least 98% identical, or at least 99% identical to the sequence set forth in SEQ ID NO: 15. The antibody may further be an IgG1 or an IgG4 isotype.

In one embodiment, the present invention is directed to an antibody, or antigen-binding fragment thereof, having the antigen binding regions of antibody C47B10-D3C. In one embodiment, the invention provides an antibody, or antigen-binding fragment thereof, comprising a heavy chain variable domain sequence as set forth in SEQ ID NO: 17, and a light chain variable domain sequence as set forth in SEQ ID NO: 15. In one embodiment, the invention is directed to an antibody having a heavy chain variable domain comprising the CDRs of SEQ ID NO: 17, and a light chain variable domain comprising the CDRs of SEQ ID NO: 15. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 17, and comprises a light chain variable region having an amino acid sequence that is at least 95% identical, at least 96% identical, at least 97% identical, at least 98% identical, or at least 99% identical to the sequence set forth in SEQ ID NO: 15. The antibody may further be an IgG1 or an IgG4 isotype.

In one embodiment, the present invention is directed to an antibody, or antigen-binding fragment thereof, having the antigen binding regions of antibody C47B10-C11C. In one embodiment, the invention provides an antibody, or antigen-binding fragment thereof, comprising a heavy chain variable domain sequence as set forth in SEQ ID NO: 18, and a light chain variable domain sequence as set forth in SEQ ID NO: 15. In one embodiment, the invention is directed to an antibody having a heavy chain variable domain comprising the CDRs of SEQ ID NO: 18, and a light chain variable domain comprising the CDRs of SEQ ID NO: 15. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 18, and comprises a light chain variable region having an amino acid sequence that is at least 95% identical, at least 96% identical, at least 97% identical, at least 98% identical, or at least 99% identical to the sequence set forth in SEQ ID NO: 15. The antibody may further be an IgG1 or an IgG4 isotype.

In one embodiment, the present invention is directed to an antibody, or antigen-binding fragment thereof, having the antigen binding regions of antibody C47K11. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 19. In one embodiment, the invention is directed to an antibody having a heavy chain variable domain comprising the CDRs of SEQ ID NO: 1, and a light chain variable domain comprising the CDRs of SEQ ID NO: 19. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 19. The antibody may further be an IgG1 or an IgG4 isotype.

In one embodiment, the present invention is directed to an antibody, or antigen-binding fragment thereof, having the antigen binding regions of antibody C47KD8. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 20. In one embodiment, the invention is directed to an antibody having a heavy chain variable domain comprising the CDRs of SEQ ID NO: 1, and a light chain variable domain comprising the CDRs of SEQ ID NO: 20. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 20. The antibody may further be an IgG1 or an IgG4 isotype.

In one embodiment, the present invention is directed to an antibody, or antigen-binding fragment thereof, having the antigen binding regions of antibody C47KD8. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 21. In one embodiment, the invention is directed to an antibody having a heavy chain variable domain comprising the CDRs of SEQ ID NO: 1, and a light chain variable domain comprising the CDRs of SEQ ID NO: 21. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 21 The antibody may further be an IgG1 or an IgG4 isotype.

In one embodiment, the present invention is directed to an antibody, or antigen-binding fragment thereof, having the antigen binding regions of antibody C47B10-H3-D4. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 19. In one embodiment, the invention is directed to an antibody having a heavy chain variable domain comprising the CDRs of SEQ ID NO: 1, and a light chain variable domain comprising the CDRs of SEQ ID NO: 19. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 19. The antibody may further be an IgG1 or an IgG4 isotype.

In one embodiment, the present invention is directed to an antibody, or antigen-binding fragment thereof, having the antigen binding regions of antibody C47B10-L1A-A10. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 23. In one embodiment, the invention is directed to an antibody having a heavy chain variable domain comprising the CDRs of SEQ ID NO: 1, and a light chain variable domain comprising the CDRs of SEQ ID NO: 23. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 23. The antibody may further be an IgG1 or an IgG4 isotype.

In one embodiment, the present invention is directed to an antibody, or antigen-binding fragment thereof, having the antigen binding regions of antibody C47B10-H3-D3. In one embodiment, the invention provides an antibody, or antigen-binding fragment thereof, comprising a heavy chain variable domain sequence as set forth in SEQ ID NO: 24, and a light chain variable domain sequence as set forth in SEQ ID NO: 8. In one embodiment, the invention is directed to an antibody having a heavy chain variable domain comprising the CDRs of SEQ ID NO: 24, and a light chain variable domain comprising the CDRs of SEQ ID NO: 8. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 24, and comprises a light chain variable region having an amino acid sequence that is at least 95% identical, at least 96% identical, at least 97% identical, at least 98% identical, or at least 99% identical to the sequence set forth in SEQ ID NO: 8. The antibody may further be an IgG1 or an IgG4 isotype.

In one embodiment, the present invention is directed to an antibody, or antigen-binding fragment thereof, having the antigen binding regions of antibody C47B10-L1A-A4. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 25. In one embodiment, the invention is directed to an antibody having a heavy chain variable domain comprising the CDRs of SEQ ID NO: 1, and a light chain variable domain comprising the CDRs of SEQ ID NO: 25. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 25. The antibody may further be an IgG1 or an IgG4 isotype.

In one embodiment, the present invention is directed to an antibody, or antigen-binding fragment thereof, having the antigen binding regions of antibody C47B10-L3-B2. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 26. In one embodiment, the invention is directed to an antibody having a heavy chain variable domain comprising the CDRs of SEQ ID NO: 1, and a light chain variable domain comprising the CDRs of SEQ ID NO: 26. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 26. The antibody may further be an IgG1 or an IgG4 isotype.

In one embodiment, the present invention is directed to an antibody, or antigen-binding fragment thereof, having the antigen binding regions of antibody C47A8-CA. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 27. In one embodiment, the invention is directed to an antibody having a heavy chain variable domain comprising the CDRs of SEQ ID NO: 1, and a light chain variable domain comprising the CDRs of SEQ ID NO: 27. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 27. The antibody may further be an IgG1 or an IgG4 isotype.

In one embodiment, the present invention is directed to an antibody, or antigen-binding fragment thereof, having the antigen binding regions of antibody C47A8-CL. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 28. In one embodiment, the invention is directed to an antibody having a heavy chain variable domain comprising the CDRs of SEQ ID NO: 1, and a light chain variable domain comprising the CDRs of SEQ ID NO: 28. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 28. The antibody may further be an IgG1 or an IgG4 isotype.

In one embodiment, the present invention is directed to an antibody, or antigen-binding fragment thereof, having the antigen binding regions of antibody C47A8-CQ. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 29. In one embodiment, the invention is directed to an antibody having a heavy chain variable domain comprising the CDRs of SEQ ID NO: 1, and a light chain variable domain comprising the CDRs of SEQ ID NO: 29. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 29. The antibody may further be an IgG1 or an IgG4 isotype.

In one embodiment, the present invention is directed to an antibody, or antigen-binding fragment thereof, having the antigen binding regions of antibody C47A8-CS. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 30. In one embodiment, the invention is directed to an antibody having a heavy chain variable domain comprising the CDRs of SEQ ID NO: 1, and a light chain variable domain comprising the CDRs of SEQ ID NO: 30. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 30. The antibody may further be an IgG1 or an IgG4 isotype.

As described in Table 5, the heavy chain variable sequences SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO. 22, SEQ ID NO: 24 and SEQ ID NO:32 share at least 95% identity to each other.

As described in Table 5, a number of light chain variable domains have amino acid sequences that are at least 95% identical to SEQ ID NO:2, including SEQ ID NO: 27 (as described for antibody C47A8-CA), SEQ ID NO: 28 (as described for antibody C47A8-CL), SEQ ID NO: 29 (as described for antibody C47A8-CQ) and SEQ ID NO: 30 (as described for antibody C47A8-CS).

A number of light chain variable domains have amino acid sequences that are at least 95% identical to SEQ ID NO:27, including SEQ ID NO: 2 (as described for antibody C47A8), SEQ ID NO: 28 (as described for antibody C47A8-CL), SEQ ID NO: 29 (as described for antibody C47A8-CQ) and SEQ ID NO: 30 (as described for antibody C47A8-CS).

A number of light chain variable domains have amino acid sequences that are at least 95% identical to SEQ ID NO:28, including SEQ ID NO: 2 (as described for antibody C47A8), SEQ ID NO: 27 (as described for antibody C47A8-CA), SEQ ID NO: 29 (as described for antibody C47A8-CQ) and SEQ ID NO: 30 (as described for antibody C47A8-CS).

A number of light chain variable domains have amino acid sequences that are at least 95% identical to SEQ ID NO:29, including SEQ ID NO: 2 (as described for antibody C47A8), SEQ ID NO: 27 (as described for antibody C47A8-CA), SEQ ID NO: 28 (as described for antibody C47A8-CL) and SEQ ID NO: 30 (as described for antibody C47A8-CS).

A number of light chain variable domains have amino acid sequences that are at least 95% identical to SEQ ID NO:30, including SEQ ID NO: 2 (as described for antibody C47A8), SEQ ID NO: 27 (as described for antibody C47A8-CA), SEQ ID NO: 28 (as described for antibody C47A8-CL) and SEQ ID NO: 29 (as described for antibody C47A8-CQ).

A number of light chain variable domains have amino acid sequences that are at least 95% identical to SEQ ID NO:8, including SEQ ID NO: 26 (as described for antibody C47B10-L3-B2), SEQ ID NO: 25 (as described for antibody C47B10-L1A-A4), SEQ ID NO: 23 (as described for antibody C47B10-L1A-A10), SEQ ID NO: 15 (as described for antibodies C47B10-C11C, C47B10-D3C, C47B10-C3C, C47B10-C6C, C47B10-B1C), SEQ ID NO: 6 (as described for antibody C47B10-1F6S), SEQ ID NO:5 (as described for antibody C47B10-1H4S), and SEQ ID NO: 4 (as described for antibody C47B10, C47B10-2B8S, C47B10-2C1S, C47B10-2B9S, C47B10-2C4S).

A number of light chain variable domains have amino acid sequences that are at least 95% identical to SEQ ID NO:4, including SEQ ID NO: 26 (as described for antibody C47B10-L3-B2), SEQ ID NO: 25 (as described for antibody C47B10-L1A-A4), SEQ ID NO: 23 (as described for antibody C47B10-L1A-A10), SEQ ID NO: 15 (as described for antibodies C47B10-C11C, C47B10-D3C, C47B10-C3C, C47B10-C6C, C47B10-B1C), SEQ ID NO: 6 (as described for antibody C47B10-1F6S), SEQ ID NO:5 (as described for antibody C47B10-1H4S), and SEQ ID NO: 8 (as described for antibody C47B10-1, C47B10-2A9S, C47B10-2B11S, C47B10-H3-D4, C47B10-H3-D3).

A number of light chain variable domains have amino acid sequences that are at least 95% identical to SEQ ID NO:5, including SEQ ID NO: 26 (as described for antibody C47B10-L3-B2), SEQ ID NO: 25 (as described for antibody C47B10-L1A-A4), SEQ ID NO: 23 (as described for antibody C47B10-L1A-A10), SEQ ID NO: 15 (as described for antibodies C47B10-C11C, C47B10-D3C, C47B10-C3C, C47B10-C6C, C47B10-B1C), SEQ ID NO: 6 (as described for antibody C47B10-1F6S), SEQ ID NO: 4 (as described for antibody C47B10, C47B10-2B8S, C47B10-2C1S, C47B10-2B9S, C47B10-2C4S) and SEQ ID NO: 8 (as described for antibody C47B10-1, C47B10-2A9S, C47B10-2B11S, C47B10-H3-D4, C47B10-H3-D3).

A number of light chain variable domains have amino acid sequences that are at least 95% identical to SEQ ID NO:6, including SEQ ID NO: 26 (as described for antibody C47B10-L3-B2), SEQ ID NO: 25 (as described for antibody C47B10-L1A-A4), SEQ ID NO: 23 (as described for antibody C47B10-L1A-A10), SEQ ID NO: 15 (as described for antibodies C47B10-C11C, C47B10-D3C, C47B10-C3C, C47B10-C6C, C47B10-B1C), SEQ ID NO:5 (as described for antibody C47B10-1H4S), SEQ ID NO: 4 (as described for antibody C47B10, C47B10-2B8S, C47B10-2C1S, C47B10-2B9S, C47B10-2C4S) and SEQ ID NO: 8 (as described for antibody C47B10-1, C47B10-2A9S, C47B10-2B11S, C47B10-H3-D4, C47B10-H3-D3).

A number of light chain variable domains have amino acid sequences that are at least 95% identical to SEQ ID NO:15, including SEQ ID NO: 26 (as described for antibody C47B10-L3-B2), SEQ ID NO: 25 (as described for antibody C47B10-L1A-A4), SEQ ID NO: 23 (as described for antibody C47B10-L1A-A10), SEQ ID NO:5 (as described for antibody C47B10-1H4S), SEQ ID NO: 6 (as described for antibody C47B10-1F6S), SEQ ID NO: 4 (as described for antibody C47B10, C47B10-2B8S, C47B10-2C1S, C47B10-2B9S, C47B10-2C4S) and SEQ ID NO: 8 (as described for antibody C47B10-1, C47B10-2A9S, C47B10-2B11S, C47B10-H3-D4, C47B10-H3-D3).

A number of light chain variable domains have amino acid sequences that are at least 95% identical to SEQ ID NO:23, including SEQ ID NO: 26 (as described for antibody C47B10-L3-B2), SEQ ID NO: 25 (as described for antibody C47B10-L1A-A4), SEQ ID NO: 15 (as described for antibodies C47B10-C11C, C47B10-D3C, C47B10-C3C, C47B10-C6C, C47B10-B1C), SEQ ID NO:5 (as described for antibody C47B10-1H4S), SEQ ID NO: 6 (as described for antibody C47B10-1F6S), SEQ ID NO: 4 (as described for antibody C47B10, C47B10-2B8S, C47B10-2C1S, C47B10-2B9S, C47B10-2C4S) and SEQ ID NO: 8 (as described for antibody C47B10-1, C47B10-2A9S, C47B10-2B11S, C47B10-H3-D4, C47B10-H3-D3).

A number of light chain variable domains have amino acid sequences that are at least 95% identical to SEQ ID NO:25, including SEQ ID NO: 26 (as described for antibody C47B10-L3-B2), SEQ ID NO: 23 (as described for antibody C47B10-L1A-A10), SEQ ID NO: 15 (as described for antibodies C47B10-C11C, C47B10-D3C, C47B10-C3C, C47B10-C6C, C47B10-B1C), SEQ ID NO:5 (as described for antibody C47B10-1H4S), SEQ ID NO: 6 (as described for antibody C47B10-1F6S), SEQ ID NO: 4 (as described for antibody C47B10, C47B10-2B8S, C47B10-2C1S, C47B10-2B9S, C47B10-2C4S) and SEQ ID NO: 8 (as described for antibody C47B10-1), C47B10-2A9S, C47B10-2B11S, C47B10-H3-D4, C47B10-H3-D3).

A number of light chain variable domains have amino acid sequences that are at least 95% identical to SEQ ID NO:26, including SEQ ID NO: 25 (as described for antibody C47B10-L1A-A4), SEQ ID NO: 23 (as described for antibody C47B10-L1A-A10), SEQ ID NO: 15 (as described for antibodies C47B10-C11C, C47B10-D3C, C47B10-C3C, C47B10-C6C, C47B10-B1C), SEQ ID NO:5 (as described for antibody C47B10-1H4S), SEQ ID NO: 6 (as described for antibody C47B10-1F6S), SEQ ID NO: 4 (as described for antibody C47B10, C47B10-2B8S, C47B10-2C1S, C47B10-2B9S, C47B10-2C4S) and SEQ ID NO: 8 (as described for antibody C47B10-1, C47B10-2A9S, C47B10-2B11S, C47B10-H3-D4, C47B10-H3-D3).

Antigen binding proteins (e.g., antibodies, antibody fragments, antibody derivatives, antibody muteins, and antibody variants) are polypeptides that bind to CD47.

Antigen-binding fragments of antigen binding proteins of the invention may be produced by conventional techniques. Examples of such fragments include, but are not limited to, Fab and F(ab')2 fragments.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

In certain embodiments, the present disclosure provides a Fab fully human antibody fragment, having a variable domain region from a heavy chain and a variable domain region from a light chain, wherein the heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO. 22, SEQ ID NO: 24, SEQ ID NO: 32, and combinations thereof, and that has a light chain variable domain sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO:23, SEQ ID NO: 25, SEQ ID NO: 26, SEQ ID NO: 27, SEQ ID NO: 28, SEQ ID NO: 29, and SEQ ID NO: 30, and combinations thereof. In one embodiment, the fully human antibody Fab fragment has both a heavy chain variable domain region and a light chain variable domain region wherein the antibody has a heavy chain/light chain variable domain sequence selected from the group consisting of SEQ ID NO: 1/SEQ ID NO: 2, SEQ ID NO: 1/SEQ ID NO: 4, SEQ ID NO: 1/SEQ ID NO: 5, SEQ ID NO:1/SEQ ID NO:8, SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO. 14/SEQ ID NO. 15, SEQ ID NO. 16/SEQ ID NO. 15, SEQ ID NO. 32/SEQ ID NO. 15, SEQ ID NO. 17/SEQ ID NO. 15, SEQ ID NO. 18/SEQ ID NO. 15, SEQ ID NO. 1/SEQ ID NO. 19, SEQ ID NO. 1/SEQ ID NO. 20, SEQ ID NO. 1/SEQ ID NO. 21, SEQ ID NO:22/SEQ ID NO:8, SEQ ID NO:1/SEQ ID NO:23, SEQ ID NO:24/SEQ ID NO:8, SEQ ID NO:1/SEQ ID NO:25, SEQ ID NO:1/SEQ ID NO:26, SEQ ID NO:1/SEQ ID NO:27, SEQ ID NO:1/SEQ ID NO:28, SEQ ID NO:1/SEQ ID NO:29 and SEQ ID NO:1/SEQ ID NO:30.

In one embodiment, the present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO. 22, SEQ ID NO: 24, and SEQ ID NO: 32, and that has a light chain variable domain sequence that is at least 95% identical to the amino acid sequence consisting of SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO: 23, SEQ ID NO: 25, SEQ ID NO: 26, SEQ ID NO: 27, SEQ ID NO: 28, SEQ ID NO: 29, and SEQ ID NO: 30. In one embodiment, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 1/SEQ ID NO. 4, SEQ ID NO. 1/SEQ ID NO. 5, SEQ ID NO:1/SEQ ID NO:8, SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO. 14/SEQ ID NO. 15, SEQ ID NO. 16/SEQ ID NO. 15, SEQ ID NO. 32/SEQ ID NO. 15, SEQ ID NO. 17/SEQ ID NO. 15, SEQ ID NO. 18/SEQ ID NO. 15, SEQ ID NO. 1/SEQ ID NO. 19, SEQ ID NO. 1/SEQ ID NO. 20, SEQ ID NO. 1/SEQ ID NO. 21, SEQ ID NO:22/SEQ ID NO:8, SEQ ID NO:1/SEQ ID NO:23, SEQ ID NO:24/SEQ ID NO:8, SEQ ID NO:1/SEQ ID NO:25, SEQ ID NO:1/SEQ ID NO:26, SEQ ID NO:1/SEQ ID NO:27, SEQ ID NO:1/SEQ ID NO:28, SEQ ID NO:1/SEQ ID NO:29, SEQ ID NO:1/SEQ ID NO:30, and combinations thereof.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSC->CPPC) (SEQ ID NOS 3 and 31, respectively) in the hinge region (Bloom et al., 1997, *Protein Science* 6:407) to alleviate a tendency to form intra-H chain disulfide bonds that can lead to heterogeneity in the IgG4 antibodies. Thus, in one embodiment, the antibody of the invention is a human IgG1 antibody. Thus, in one embodiment, the antibody of the invention is a human IgG4 antibody.

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)). Near et al. *Mol. Immunol.* 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2). Thus, the invention also includes, in certain embodiments, variable sequences having at least 95% identity to those sequences disclosed herein.

In certain embodiments, an anti-CD47 antibody, or antigen-binding fragment thereof, provided herein has a dissociation constant ($K_D$) of $1 \times 10^{-6}$ M or less; $5 \times 10^{-7}$ M or less, $1 \times 10^{-7}$ M or less; $5 \times 10^{-8}$ M or less; $1 \times 10^{-8}$ M or less; $5 \times 10^{-9}$ M or less; or $1 \times 10^{-9}$ M or less. In one embodiment, the antibody, or antigen-binding fragment thereof, of the invention as a $K_D$ from $1 \times 10^{-7}$ M to $1 \times 10^{-10}$ M. In one embodiment, the antibody, or antigen-binding fragment thereof, of the invention as a $K_D$ from $1 \times 10^{-8}$ M to $1 \times 10^{-10}$ M.

Those of ordinary skill in the art will appreciate standard methods known for determining the $K_D$ of an antibody, or fragment thereof. For example, in one embodiment, $K_D$ is measured by a radiolabeled antigen binding assay (RIA). In one embodiment, an RIA is performed with the Fab version of an antibody of interest and its antigen, e.g., human CD47. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). According to another embodiment, $K_D$ is measured using a BIACORE surface plasmon resonance assay. The term "surface plasmon resonance", as used herein, refers to an optical phenomenon that allows for the analysis of real-time interactions by detection of alterations in protein concentrations within a biosensor matrix, for example using the BIACORE system (Biacore Life Sciences division of GE Healthcare, Piscataway, N.J.).

In particular embodiments, antigen binding proteins of the present invention have a binding affinity ($K_a$) for CD47 of at least $10^6$ M$^{-1}$. In other embodiments, the antigen binding proteins exhibit a $K_a$ of at least $10^7$ M$^{-1}$, at least $10^8$ M$^{-1}$, at least $10^9$ M$^{-1}$, or at least $10^{10}$M$^{-1}$. In another embodiment, the antigen binding protein exhibits a $K_a$ substantially the same as that of an antibody described herein in the Examples.

In another embodiment, the present disclosure provides an antigen binding protein that has a low dissociation rate from CD47. In one embodiment, the antigen binding protein has a $K_{off}$ of $1 \times 10^{-4}$ to $^{-1}$ sec$^{-1}$ or lower. In another embodiment, the $K_{off}$ is $5 \times 10^{-5}$ to $^{-1}$ sec$^{-1}$ or lower. In another embodiment, the $K_{off}$ is substantially the same as an antibody described herein. In another embodiment, the antigen binding protein binds to CD47 with substantially the same $K_{off}$ as an antibody described herein.

In another aspect, the present disclosure provides an antigen binding protein that inhibits an activity of CD47. In one embodiment, the antigen binding protein has an IC$_{50}$ of 1000 nM or lower. In another embodiment, the IC$_{50}$ is 100 nM or lower; in another embodiment, the IC$_{50}$ is 10 nM or lower. In another embodiment, the IC$_{50}$ is substantially the same as that of an antibody described herein in the Examples. In another embodiment, the antigen binding protein inhibits an activity of CD47 with substantially the same $IC_{50}$ as an antibody described herein.

In another aspect, the present disclosure provides an antigen binding protein that binds to CD47 expressed on the surface of a cell and, when so bound, inhibits CD47 signaling activity in the cell without causing a significant reduction in the amount of CD47 on the surface of the cell. Any method for determining or estimating the amount of CD47 on the surface and/or in the interior of the cell can be used. In other embodiments, binding of the antigen binding protein to the CD47-expressing cell causes less than about 75%, 50%, 40%, 30%, 20%, 15%, 10%, 5%, 1%, or 0.1% of the cell-surface CD47 to be internalized.

In one embodiment, the anti-CD47 antibodies, and antibody fragments, described herein bind to CD47 and promote macrophage mediated phagocytosis of tumor cells expressing CD47. Phagocytosis by macrophages relies on the cell's recognition of prophagocytic ("eat me") and antiphagocytic ("don't eat me") signals on target cells. Anti-CD47 blocking antibodies and antibody fragments, such as those described herein, induce macrophage phagocytosis of cancer cells by inhibiting an antiphagocytic signal, allowing prophagocytic signals to dominate (Majeti et al. (2009) *Cell* 138(2):286-299; Willingham et al. (2012) *Proc Natl Acad Sci USA* 109(17):6662-6667). Thus, in one embodiment, an antibody or an antibody fragment disclosed herein prevents CD47 from interacting with the CD47 ligand, SIRPα.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half-life, such as described in WO00/09560, incorporated by reference herein.

The present disclosure further provides multi-specific antigen binding proteins, for example, bispecific antigen binding proteins, e.g., antigen binding protein that bind to two different epitopes of CD47, or to an epitope of CD47 and an epitope of another molecule, via two different antigen binding sites or regions. Moreover, bispecific antigen binding protein as disclosed herein can comprise a CD47 binding site from one of the herein-described antibodies and a second CD47 binding region from another of the herein-described antibodies, including those described herein by reference to other publications. Alternatively, a bispecific antigen binding protein may comprise an antigen binding site from one of the herein described antibodies and a second antigen binding site from another CD47 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Oligomers that contain one or more antigen binding proteins may be employed as CD47 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have CD47 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing a CD47 binding fragment of an anti-CD47 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-CD47 antibody fragment or derivative fused to a leucine zipper peptide are expressed in suitable host cells, and the soluble oligomeric anti-CD47 antibody fragments or derivatives that form are recovered from the culture supernatant.

Antigen binding proteins directed against CD47 can be used, for example, in assays to detect the presence of CD47 polypeptides, either in vitro or in vivo. The antigen binding proteins also may be employed in purifying CD47 proteins by immunoaffinity chromatography. Blocking antigen binding proteins can be used in the methods disclosed herein. Such antigen binding proteins that function as CD47 antagonists may be employed in treating any CD47-induced condition, including but not limited to various cancers.

Antigen binding proteins may be employed in an in vitro procedure, or administered in vivo to inhibit CD47-induced biological activity. Disorders that would benefit (directly or indirectly), for example, from proteolytic activation of CD47, examples of which are provided herein, thus may be treated.

In one embodiment, the present invention provides a therapeutic method comprising in vivo administration of a CD47 blocking antigen binding protein to a mammal in need thereof in an amount effective for reducing a CD47-induced biological activity.

In certain embodiments of the invention, antigen binding proteins include fully human monoclonal antibodies that inhibit a biological activity of CD47, such as binding of CD47 to SIRPα.

Antigen binding proteins, including antibodies and antibody fragments described herein, may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides, including antibodies and antibody fragments described herein, of the invention.

In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N. Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of CD47 bound thereto. Polypeptides contemplated for use herein include substantially homogeneous recombinant mammalian anti-CD47 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-CD47 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA.* 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N. Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells. Suitable bacteria include gram negative or gram positive organisms, for example, E. coli or Bacillus spp. Yeast, preferably from the Saccharomyces species, such as S. cerevisiae, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in E. coli as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system. CD47-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis. The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis. The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

In certain embodiments, the present disclosure provides monoclonal antibodies that bind to CD47. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, Science 253:164.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. Biochemistry. 2001 31; 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$—CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life (t$_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Methods, Formulations, and Modes of Administration

In certain embodiments, the present disclosure further provides a method for treating a broad spectrum of mammalian cancers or a broad spectrum of fibrotic diseases, requiring either stimulation of immune responses or suppression, comprising administering an anti-CD47 polypeptide. Any of the antibodies disclosed herein may be used in such methods. For example, the methods may be performed using an anti-CD47 polypeptide selected from the group consisting of a fully human antibody of an IgG class that binds to a CD47 epitope with a binding affinity of at least 10$^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, including the heavy and light chain variable regions (and CDRs within said sequences) described in SEQ ID Nos. 1-32 (Table 5).

For example, in one embodiment, the methods disclosed herein include the use of an anti-CD47 fully human antibody having a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO. 22, SEQ ID NO: 24 and SEQ ID NO: 32, and that has a light chain variable domain sequence that is at least 95% identical, at least 96% identical, at least 97% identical, at least 98% identical, or at least 99% identical, to the amino acid sequences selected from the group consisting of SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO:23, SEQ ID NO: 25, SEQ ID NO: 26, SEQ ID NO: 27, SEQ ID NO: 28, SEQ ID NO: 29, and SEQ ID NO: 30.

In one embodiment, the methods described herein include the use of an anti-CD47 fully human Fab antibody fragment has the heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO. 22, SEQ ID NO: 24 and SEQ ID NO: 32, and that has the light chain variable domain sequence that is at least 95% identical, at least 96% identical, at least 97% identical, at least 98% identical, or at least 99% identical, to the amino acid sequence consisting SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO:23, SEQ ID NO: 25, SEQ ID NO: 26, SEQ ID NO: 27, SEQ ID NO: 28, SEQ ID NO: 29, and SEQ ID NO: 30; and In one embodiment, the methods described herein include the use of an anti-CD47 single chain human antibody having a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 7, SEQ ID NO. 9, SEQ ID NO. 10, SEQ ID NO. 11, SEQ ID NO. 12, SEQ ID NO. 13, SEQ ID NO. 14, SEQ ID NO. 16, SEQ ID NO. 17, SEQ ID NO. 18, SEQ ID NO. 22, SEQ ID NO: 24 and SEQ ID NO: 32, and that has the light chain variable domain sequence that is at least 95% identical, at least 96% identical, at least 97% identical, at least 98% identical, or at least 99% identical, to an amino acid sequence consisting of SEQ ID NO. 2, SEQ ID NO. 4, SEQ ID NO. 5, SEQ ID NO. 6, SEQ ID NO. 8, SEQ ID NO. 15, SEQ ID NO: 19, SEQ ID NO. 20, SEQ ID NO. 21, SEQ ID NO:23, SEQ ID NO: 25, SEQ ID NO: 26, SEQ ID NO: 27, SEQ ID NO: 28, SEQ ID NO: 29, and SEQ ID NO: 30.

In one embodiment, the anti-CD47 fully human antibody has both a heavy chain and a light chain wherein the antibody has a heavy chain/light chain variable domain sequence selected from the group consisting of SEQ ID NO: 1/SEQ ID NO: 2, SEQ ID NO: 1/SEQ ID NO: 4, SEQ ID NO: 1/SEQ ID NO: 5, SEQ ID NO:1/SEQ ID NO:8, SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO. 14/SEQ ID NO. 15, SEQ ID NO. 16/SEQ ID NO. 15, SEQ ID NO. 32/SEQ ID NO. 15, SEQ ID NO. 17/SEQ ID NO. 15, SEQ ID NO. 18/SEQ ID NO. 15, SEQ ID NO. 1/SEQ ID NO. 19, SEQ ID NO. 1/SEQ ID NO. 20, SEQ ID NO. 1/SEQ ID NO. 21, SEQ ID NO:22/SEQ ID NO:8, SEQ ID NO:1/SEQ ID NO:23, SEQ ID NO:24/SEQ ID NO:8, SEQ ID NO:1/SEQ ID NO:25, SEQ ID NO:1/SEQ ID NO:26, SEQ ID NO:1/ SEQ ID NO:27, SEQ ID NO:1/SEQ ID NO:28, SEQ ID NO:1/SEQ ID NO:29, and SEQ ID NO:1/SEQ ID NO:30.

In one embodiment, the anti-CD47 fully human antibody Fab fragment has both a heavy chain variable domain region and a light chain variable domain region wherein the antibody has a heavy chain/light chain variable domain sequence selected from the group consisting of SEQ ID NO: 1/SEQ ID NO: 2, SEQ ID NO: 1/SEQ ID NO: 4, SEQ ID NO: 1/SEQ ID NO: 5, SEQ ID NO:1/SEQ ID NO:8, SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO. 14/SEQ ID NO. 15, SEQ ID NO. 16/SEQ ID NO. 15, SEQ ID NO. 32/SEQ ID NO. 15, SEQ ID NO. 17/SEQ ID NO. 15, SEQ ID NO. 18/SEQ ID NO. 15, SEQ ID NO. 1/SEQ ID NO. 19, SEQ ID NO. 1/SEQ ID NO. 20, SEQ ID NO. 1/SEQ ID NO. 21, SEQ ID NO:22/SEQ ID NO:8, SEQ ID NO:1/SEQ ID NO:23, SEQ ID NO:24/SEQ ID NO:8, SEQ ID NO:1/SEQ ID NO:25, SEQ ID NO:1/SEQ ID NO:26, SEQ ID NO:1/ SEQ ID NO:27, SEQ ID NO:1/SEQ ID NO:28, SEQ ID NO:1/SEQ ID NO:29, and SEQ ID NO:1/SEQ ID NO:30.

In one embodiment, the anti-CD47 fully human single chain antibody has both a heavy chain variable domain region and a light chain variable domain region, wherein the single chain fully human antibody has a heavy chain/light chain variable domain sequence selected from the group consisting of SEQ ID NO: 1/SEQ ID NO: 2, SEQ ID NO: 1/SEQ ID NO: 4, SEQ ID NO: 1/SEQ ID NO: 5, SEQ ID NO:1/SEQ ID NO:8, SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO. 14/SEQ ID NO. 15, SEQ ID NO. 16/SEQ ID NO. 15, SEQ ID NO. 32/SEQ ID NO. 15, SEQ ID NO. 17/SEQ ID NO. 15, SEQ ID NO. 18/SEQ ID NO. 15, SEQ ID NO. 1/SEQ ID NO. 19, SEQ ID NO. 1/SEQ ID NO. 20, SEQ ID NO. 1/SEQ ID NO. 21, SEQ ID NO:22/ SEQ ID NO:8, SEQ ID NO:1/SEQ ID NO:23, SEQ ID NO:24/SEQ ID NO:8, SEQ ID NO:1/SEQ ID NO:25, SEQ ID NO:1/SEQ ID NO:26, SEQ ID NO:1/SEQ ID NO:27, SEQ ID NO:1/SEQ ID NO:28, SEQ ID NO:1/SEQ ID NO:29, and SEQ ID NO:1/SEQ ID NO:30.

CD47 is highly expressed on cancer cells as compared with normal cells (Majeti et al. (2009) *Cell* 138(2):286-299; Willingham et al. (2012) *Proc Natl Acad Sci USA* 109(17): 6662-6667), and interacts with the ligand signal regulatory protein α (SIRP-α) on macrophages (Brown and Frazier (2001) *Trends Cell Biol* 11(3):130-135).

Thus, in one embodiment, the anti-CD47 antibodies and antibody fragments of the invention are used to treat a broad spectrum of mammalian cancers. In one embodiment, the anitbodies and antibody fragments described herein are used to treated cancer, including ovarian, colon, breast, lung cancers, myelomas, neuroblastic-derived CNS tumors, monocytic leukemias, B-cell derived leukemias, T-cell derived leukemias, B-cell derived lymphomas, T-cell derived lymphomas, mast cell derived tumors, and combinations thereof.

In one embodiment the anti-CD47 antibodies described herein are useful in treating, delaying the progression of, preventing relapse of or alleviating a symptom of a cancer or other neoplastic condition, including, hematological malignancies and/or CD47+ tumors.

In one embodiment, a human subject having a tumor overexpressing CD47 is treated with an anti-CD47 antibody, or antibody fragment, disclosed herein. In one embodiment, the methods disclosed herein are used to treat a subject having a solid tumor associated with aberrant, e.g., overexpression, CD47 expression, activity or signaling. Solid tumors include, e.g., breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

The CD47 antibodies described herein are useful in treating a cancer selected from the group consisting of B-cell derived lymphomas, T-cell derived lymphomas, non-Hodgkin's lymphoma (NHL), acute lymphocytic leukemia (ALL), acute myeloid leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, and solid tumors, wherein solid tumors are selected from the group consisting of breast tumors, ovarian tumors, lung tumors, pancreatic tumors, prostate tumors, melanoma tumors, colorectal tumors, lung tumors, head and neck tumors, bladder tumors, esophageal tumors, liver tumors, kidney tumors, neuroblastic-derived CNS tumors, and mast cell derived tumors.

In one embodiment, the anti-CD47 antibodies and antibody fragments of the invention are used to treat a broad spectrum of fibrotic diseases. For example, in one embodiment, the fibrotic disease to be treated is selected from the group consisting of myocardial infarction, angina, osteoarthritis, pulmonary fibrosis, asthma, cystic fibrosis, bronchitis, asthma, and combinations thereof.

The present disclosure features methods for treating or preventing the *S. aureus* infection comprising administering an anti-CD47 polypeptide. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

In certain embodiments, the disclosed antibodies are administered by inhalation, but aerosolization of full IgG antibodies may prove limiting due to their molecular size (~150 kDa). To maximize available commercial aerosolization devices, smaller Fab fragments may be required.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

A CD47 binding polypeptide, as disclosed herein, can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-CD47 antibodies agents of the invention can be used alone.

In certain embodiments, the binding polypeptides of fragments thereof can be labeled or unlabeled for diagnostic purposes. Typically, diagnostic assays entail detecting the formation of a complex resulting from the binding of a binding polypeptide to CD47. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a CD47 protein is combined with the subject binding polypeptides, binding occurs between the binding polypeptides and the CD47 protein. In one embodiment, a sample containing cells expressing a CD47 protein (e.g., endothelial cells) is combined with the subject antibodies, and binding occurs between the binding polypeptides and cells bearing a CD47 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a CD47 protein in a biological sample can also be prepared. Such kits will include a CD47 binding polypeptide which binds to a CD47 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin) For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

EXAMPLE 1

Heavy and light chain variable domain amino acid sequences from human anti-CD47 antibodies were identified, including antibodies C47B10, C47A8, C47A11, and C47D8. The heavy and light chain variable domain sequences of these antibodies are described in Table 5 below (Table 5 is a summary of all sequences disclosed herein).

The following example describes anti-CD47 antibody-mediated phagocytosis of cancer by macrophages. Specifically, the functional activity of antibodies A8, B10, A11, and D8 against CD47 was determined by measuring their ability to promote macrophage mediated phagocytosis of tumor cells.

Macrophages were prepared by culturing purified CD14 positive monocytes in medium containing macrophage colony stimulating factor (M-CSF) at 30 ng/ml. After 5 days of culture the cells exhibited the characteristics of macrophages and were used in the phagocytosis assay. On the day prior to the phagocytosis assay, K562 target cells (a human myelogenous leukemia line) were labeled with CFSE (carboxyfluorescein succinimidyl ester). On the day of assay, target cells were pre-incubated with the test antibodies at 1 microgram per milliliter. After 15 minutes, the cells were washed and added to the macrophages at a ratio of two macrophages to one target cell. After three hours at 37° C., the cells were stained with phycoerythrin conjugated anti-CD11b and incubated a further 15 minutes. The cells were then removed from the wells and analyzed by flow cytometry.

FIG. 1 provides data demonstrating the ability of anti-CD47 antibodies, but not the control antibody (an isotype matched negative control antibody, i.e. an antibody that not only does not bind CD47, but also not bind to the cells), to promote the phagocytosis of K562 cancer cells. The cell populations in the upper right quadrant of FIG. 1 represent the macrophages with phagocytosed K562 cells. The cells in the lower right quadrant are the K562 cells which have not been phagocytosed. All the anti-CD47 antibodies tested exhibited some activity, with C47B10 (referred to as B10 in FIG. 1) promoting the most phagocytosis.

EXAMPLE 2

Germline mutation of the C47B10 antibody (or "B10" antibody) was carried out to increase stability and reduce risk of immunogenicity. Germlining of the B10 antibody involved changing certain framework residues to match the germline sequence. When compared to the germline sequence, the third amino acid of the light chain was different from the germline sequence. This was identified using known germline databases. Thus, the third amino acid in the light chain of the B10 antibody was changed from V to A. Table 1 below shows the C47B10 wild type sequence (SEQ ID NO:1/SEQ ID NO:4) and the C47B10-1 germline changed sequence (SEQ ID NO:1/SEQ ID NO:8).

TABLE 1

| Name | Heavy Chain variable domain region | Light Chain variable domain region |
|---|---|---|
| C47B10 | QVQLVQSGAEVKKPGASVKVSC KASGYTFTSYYMHWVRQAPGQ GLEWMGIINPSGGSTSYAQKFQG RVTMTRDTSTSTVYMELSSLRSE DTAVYYCARSTLWFSEFDYWGQ GTLVTVSS SEQ ID NO. 1 | QSVLTQPASVSGSPGQSISISCTGTSS DVGGHNYVSWYQQHPGKAPKLMIY DVRNRPSGVSNRFSGSKSGSTASLTIS GLQTEDEADYYCNSYTGSRTYVFGS GTKLTVL SEQ ID NO. 4 |
| C47B10-1 | QVQLVQSGAEVKKPGASVKVSC KASGYTFTSYYMHWVRQAPGQ GLEWMGIINPSGGSTSYAQKFQG RVTMTRDTSTSTVYMELSSLRSE DTAVYYCARSTLWFSEFDYWGQ GTLVTVSS (SEQ ID NO: 1) | QSALTQPASVSGSPGQSISISCTGTSS DVGGHNYVSWYQQHPGKAPKLMIY DVRNRPSGVSNRFSGSKSGSTASLTIS GLQTEDEADYYCNSYTGSRTYVFGS GTKLTVL (SEQ ID NO: 8) |

EXAMPLE 3

Improved C47B10 Antibodies

C47B10-1 was used as the parent antibody for further mutation in an effort to improve affinity characteristics. Briefly, single amino acids within the CDRs (defined by either Chothia or Kabat numbering) of C47B10-1 (note that C47B10 and C47B10-1 antibodies have the same CDRs as they differ only by one framework residue in the light chain variable region) were mutated such that each position within each CDR was mutated to all possible 20 amino acids. These B10 variant antibodies were then screened for affinity changes relative to the C47B10-1 parent antibody and antibodies that showed differences in binding were sequenced. Certain variants were identified which showed poorer affinity for CD47 relative to C47B10-1. These lower affinity variants only had single mutations relative to C47B10-1 and were identified as antibodies C47B10 H3-D4, C47B10 L1A-A10, C47B10H3-D3, C47B10 L1A-A4, and C47B10L3-B2. Antibodies C47B10H3-D4 and C47B10L1A-A10 showed the lowest affinity of the variants selected and tested according to ELISA (described in more detail below). Hits having increased affinity were also sequenced and included in a combinatorial library, which was then expressed and screened for even further improved affinity antibodies. The light and heavy chain variable domain amino acid sequences of C47B10-1 variants (increased and decreased affinity variants; those not mentioned above are higher affinity variants) are described below in Table 2.

TABLE 2

| | Heavy chain variable domain regions | Light chain variable domain regions |
|---|---|---|
| C47B10-H3-D4 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWVSEF DYWGQGTLVTVSS (SEQ ID NO: 22) | QSALTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL (SEQ ID NO: 8) |
| C47B10-L1A-A10 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS (SEQ ID NO: 1) | QSALTQPASVSGSPGQSISISCTG TSSDVGWHNYVSWYQQHPGKA PKLMIYDVRNRPSGVSNRFSGSK SGSTASLTISGLQTEDEADYYCN SYTGSRTYVFGSGTKLTVL (SEQ ID NO: 23) |
| C47B10-H3-D3 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DWWGQGTLVTVSS (SEQ ID NO: 24) | QSALTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL (SEQ ID NO: 8) |
| C47B10-L1A-A4 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS (SEQ ID NO: 1) | QSALTQPASVSGSPGQSISISCTG TSSDVVGHNYVSWYQQHPGKAP KLMIYDVRNRPSGVSNRFSGSKS GSTASLTISGLQTEDEADYYCNS YTGSRTYVFGSGTKLTVL (SEQ ID NO: 25) |
| C47B10-L3-B2 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS (SEQ ID NO: 1) | QSALTQPASVSGSPGQSISISCTG TSSDVGGHNYVSWYQQHPGKAP KLMIYDVRNRPSGVSNRFSGSKS GSTASLTISGLQTEDEADYYCTS YTGSRTYVFGSGTKLTVL (SEQ ID NO: 26) |
| C47B10-1H4S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO. 1 | QSALTQPASVSGSPGQSISISCTG TSVDVGGHNYVSWYQQHPGKA PKLMIYDVRNRPSGVSNRFSGSK SGSTASLTISGLQTEDEADYYCN SYTGSRTYVFGSGTKLTVL SEQ ID NO. 5 |
| C47B10-1F6S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO. 1 | QSALTQPASVSGSPGQSISISCTG TSSDVGGHNYVSWYQQHPGKAP KLMIYDVRNRPSGVSNRFSGSKS GSTASLTISGLQTEDEADYYCLS YTGSRTYVFGSGTKLTVL SEQ ID NO. 6 |
| C47B10-2A9S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSRLWFSEF DYWGQGTLVTVSS SEQ ID NO. 7 | QSALTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL SEQ ID NO. 8 |
| C47B10-2B11S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSKLWFSEF DYWGQGTLVTVSS SEQ ID NO. 9 | QSALTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL SEQ ID NO. 8 |
| C47B10-2B8S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWYSEF DYWGQGTLVTVSS SEQ ID NO. 10 | QSVLTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL SEQ ID NO. 4 |

TABLE 2-continued

| | Heavy chain variable domain regions | Light chain variable domain regions |
|---|---|---|
| C47B10-2C1S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFTEF DYWGQGTLVTVSS SEQ ID NO. 11 | QSVLTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL SEQ ID NO. 4 |
| C47B10-2B9S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSAF DYWGQGTLVTVSS SEQ ID NO. 12 | QSVLTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL SEQ ID NO. 4 |
| C47B10-2C4S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSSF DYWGQGTLVTVSS SEQ ID NO. 13 | QSVLTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL SEQ ID NO. 4 |
| C47B10-B1C | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSRLWYTE FDYWGQGTLVTVSS SEQ ID NO. 14 | QSALTQPASVSGSPGQSISISCTG TSVDVGGHNYVSWYQQHPGKA PKLMIYDVRNRPSGVSNRFSGSK SGSTASLTISGLQTEDEADYYCLS YTGSRTYVFGSGTKLTVL SEQ ID NO. 15 |
| C47B10-C6C | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSRLWYTA FDYWGQGTLVTVSS SEQ ID NO. 16 | QSALTQPASVSGSPGQSISISCTG TSVDVGGHNYVSWYQQHPGKA PKLMIYDVRNRPSGVSNRFSGSK SGSTASLTISGLQTEDEADYYCLS YTGSRTYVFGSGTKLTVL SEQ ID NO. 15 |
| C47B10-C3C | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSKLWYTA FDYWGQGTLVTVSS SEQ ID NO. 32 | QSALTQPASVSGSPGQSISISCTG TSVDVGGHNYVSWYQQHPGKA PKLMIYDVRNRPSGVSNRFSGSK SGSTASLTISGLQTEDEADYYCLS YTGSRTYVFGSGTKLTVL SEQ ID NO. 15 |
| C47B10-D3C | QVQLVQSGAEVKKPGASVKVSCKASGY TFTSYYMHWVRQAPGQGLEWMGIINP SGGSTSYAQKFQGRVTMTRDTSTSTV YMELSSLRSEDTAVYYCARSKLWYTE FDYWGQGTLVTVSS SEQ ID NO. 17 | QSALTQPASVSGSPGQSISISCTG TSVDVGGHNYVSWYQQHPGKA PKLMIYDVRNRPSGVSNRFSGSK SGSTASLTISGLQTEDEADYYCLS YTGSRTYVFGSGTKLTVL SEQ ID NO. 15 |
| C47B10-C11C | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSRLWYSE FDYWGQGTLVTVSS SEQ ID NO. 18 | QSALTQPASVSGSPGQSISISCTG TSVDVGGHNYVSWYQQHPGKA PKLMIYDVRNRPSGVSNRFSGSK SGSTASLTISGLQTEDEADYYCLS YTGSRTYVFGSGTKLTVL SEQ ID NO. 15 |

Hemagglutination testing can be used as a measure for side effects of a therapeutic antibody given that hemagglutination in vivo can result in acute anemia and should be avoided. As such, an in vitro hemagglutination assay was used to determine to test the activity of the above B10 variant antibodies in serum. Briefly, human red blood cells were diluted to a 20% solution in PBS and 100 microliters of this solution was added to the wells of a 96 well round bottom plate. Serial dilutions (100 microliters) of test antibodies in PBS were added to these wells and mixed with the red blood cells. No antibody and isotype matched non-CD47 binding antibody were used as controls. The plate was incubated overnight at 37° C. and was evaluated visually the following day for agglutination (which is the formation of a blood cell button). The lower affinity antibodies C47B10 H3-D4, C47B10 L1A-A10, C47B10H3-D3, C47B10 L1A-A4, and C47B10L3-B2 showed lower levels of hemagglutination relative to the C47B10 variant antibodies having higher affinity relative to parent antibody C47B10-1.

Improved C47A8 Antibodies

Improved antibodies were also generated from the C47A8 antibody. C47A8 was selected because it showed low hemagglutination in the in vitro hemagglutination assay (described above).

C47A8 has an unpaired cysteine in its light chain CDR3 domain. This cysteine was removed with a series of point mutations at that position in order to preserve affinity from the parent C47A8 antibody. The original C47A8 sequence and variants for C47A8 are described below in Table 3. The amino acid change from cysteine to A/L/Q/or S are highlighted in bold in Table 3 in the light chain.

TABLE 3

| Name | Heavy Chain | Light Chain |
|---|---|---|
| C47A8 | QVQLVQSGAEVKKPGASVKVS CKASGYTFTSYYMHWVRQAPG QGLEWMGIINPSGGSTSYAQKF QGRVTMTRDTSTSTVYMELSSL RSEDTAVYYCARSTLWFSEFDY WGQGTLVTVSS SEQ ID NO. 1 | QSVLTQPSSVSASPGQSITISCSGTSSD VGGHNYVSWYQQHPGKAPKLMIYD VTKRPSGVPDRFSGSKSGNTASLTVS GLQAEDEADYYCCSYAGSRVYVFGT GTKLTVL SEQ ID NO. 2 |
| C47A8-CA | QVQLVQSGAEVKKPGASVKVS CKASGYTFTSYYMHWVRQAPG QGLEWMGIINPSGGSTSYAQKF QGRVTMTRDTSTSTVYMELSSL RSEDTAVYYCARSTLWFSEFDY WGQGTLVTVSS (SEQ ID NO: 1) | QSVLTQPSSVSASPGQSITISCSGTSSD VGGHNYVSWYQQHPGKAPKLMIYD VTKRPSGVPDRFSGSKSGNTASLTVS GLQAEDEADYYCASYAGSRVYVFGT GTKLTVL (SEQ ID NO: 27) |
| C47A8-CL | QVQLVQSGAEVKKPGASVKVS CKASGYTFTSYYMHWVRQAPG QGLEWMGIINPSGGSTSYAQKF QGRVTMTRDTSTSTVYMELSSL RSEDTAVYYCARSTLWFSEFDY WGQGTLVTVSS SEQ ID NO: 1) | QSVLTQPSSVSASPGQSITISCSGTSSD VGGHNYVSWYQQHPGKAPKLMIYD VTKRPSGVPDRFSGSKSGNTASLTVS GLQAEDEADYYCLSYAGSRVYVFGT GTKLTVL (SEQ ID NO: 28) |
| C47A8-CQ | QVQLVQSGAEVKKPGASVKVS CKASGYTFTSYYMHWVRQAPG QGLEWMGIINPSGGSTSYAQKF QGRVTMTRDTSTSTVYMELSSL RSEDTAVYYCARSTLWFSEFDY WGQGTLVTVSS (SEQ ID NO: 1) | QSVLTQPSSVSASPGQSITISCSGTSSD VGGHNYVSWYQQHPGKAPKLMIYD VTKRPSGVPDRFSGSKSGNTASLTVS GLQAEDEADYYCQSYAGSRVYVFGT GTKLTVL (SEQ ID NO: 29) |
| C47A8-CS | QVQLVQSGAEVKKPGASVKVS CKASGYTFTSYYMHWVRQAPG QGLEWMGIINPSGGSTSYAQKF QGRVTMTRDTSTSTVYMELSSL RSEDTAVYYCARSTLWFSEFDY WGQGTLVTVSS (SEQ ID NO: 1) | QSVLTQPSSVSASPGQSITISCSGTSSD VGGHNYVSWYQQHPGKAPKLMIYD VTKRPSGVPDRFSGSKSGNTASLTVS GLQAEDEADYYCSSYAGSRVYVFGT GTKLTVL (SEQ ID NO: 30) |

EXAMPLE 4

Figure 2:
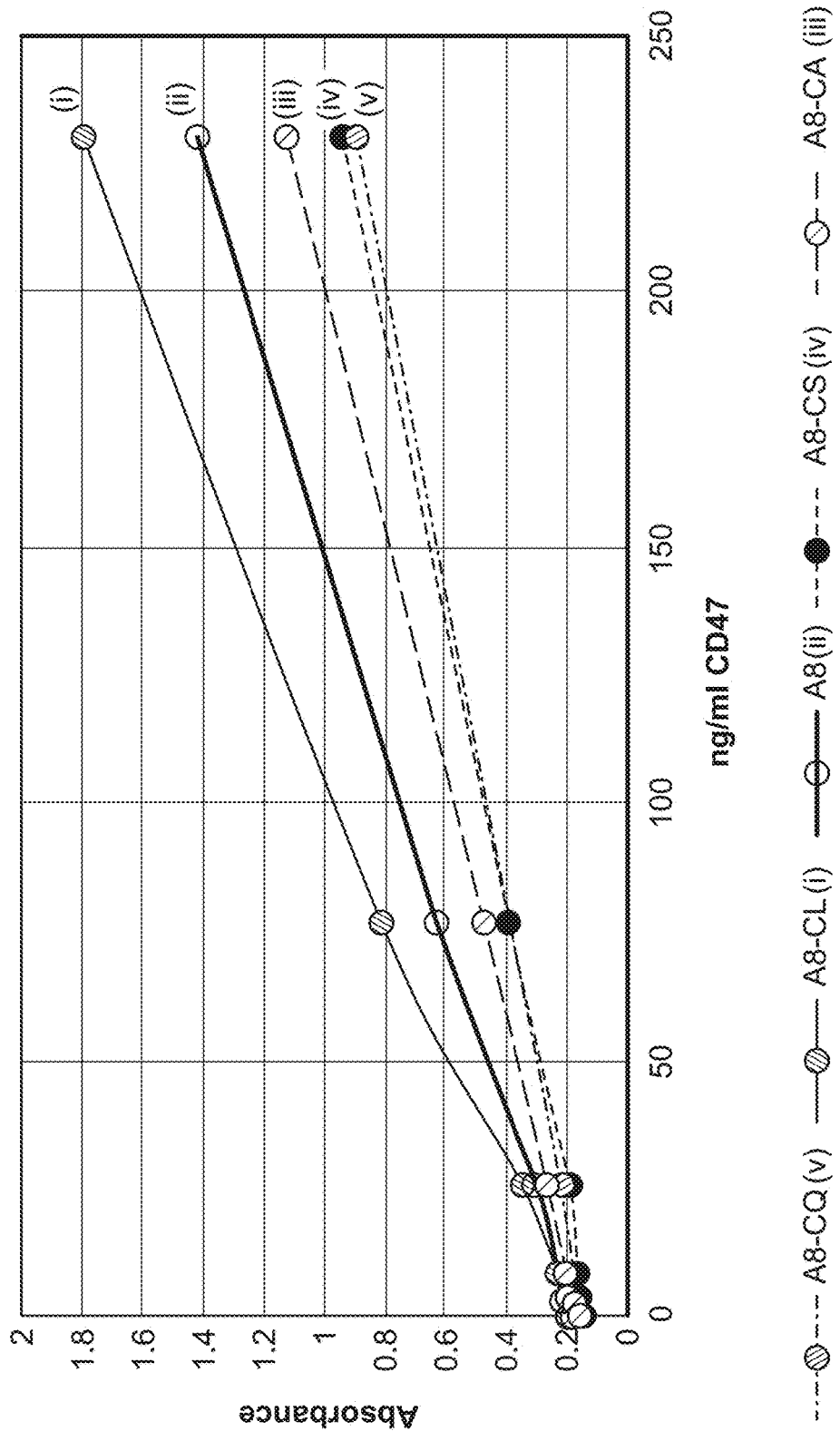
FIG. 2 shows results of an ELISA assay used to determine the binding specificity of antibodies A8 and certain A8 variants (A8-CL, A8-CA, A8-CS, A8-CQ) to CD47.

An ELISA was done to assess binding of antibodies C47A8 and C47A8 variants (shown in Table 3) to human CD47. An ELISA plate was coated overnight at 4° C. with 1 µg/ml goat anti-human $F_D$ antibody in PBS. The next day the plate was blocked with casein for 1.5 h, washed and the anti-CD47 IgG antibodies added at 1 µg/ml in casein for 2 h. Biotinylated CD47 was pre-complexed with neutravidin-AP for 20 minutes, serially diluted in casein and added to the ELISA plate. After 1 h incubation at room temperature, the plate was washed, developed with p-nitrophenyl phosphate (PNPP) substrate and the absorbance was measured. The results are shown in FIG. 2. As shown in FIG. 2, C47A8-CL bound more CD47 receptor than C47A8. Under these conditions, C47 A8-CL appeared to have better binding to antigen compared to C47 A8, while the other antibodies had slightly less affinity to CD47 antigen than did parent antibody C47A8.

Figure 3:
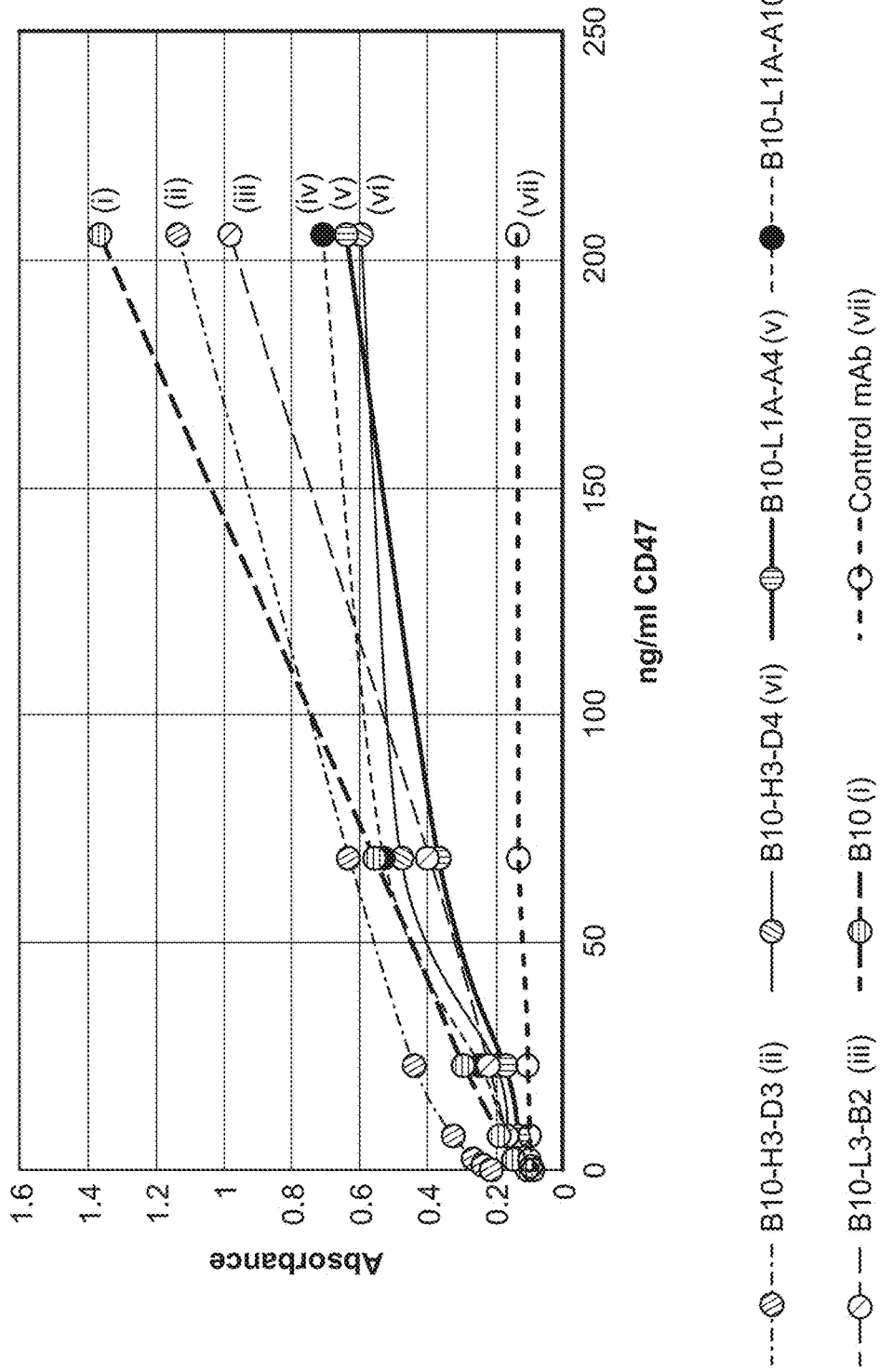
FIG. 3 shows results of an ELISA assay used to determine the binding specificity of antibodies B10 and B10 variants (B10-H3-D3, B10-L3-B2, B10-H3-D4, B-10-L1A-A4, B10-L1A-A10) to CD47.

An ELISA was also done to assess the binding of selected C47B10 variants to human CD47. The ELISA plate was coated with 1 µg/ml goat anti-human lambda antibody in PBS overnight at 4° C. The next day the plate was blocked for 1.5 h with casein. The antibodies were added at 1.3 µg/ml in casein and incubated at room temperature for 4 h. After washing, serially diluted biotinylated CD47 pre-complexed with neutravidin-AP was added and incubated at room temperature for 1 h. After washing, the plate was incubated with PBS-Tween for 20 min before being washed, developed with PNPP substrate and the absorbance measured. The results are shown in FIG. 3. As shown in FIG. 3, these B10 variants all demonstrated less affinity to human CD47 than the C47B10 antibody. Under these conditions, the mutated antibodies appear to have weaker binding to antigen compared to C47B10.

Figure 4:
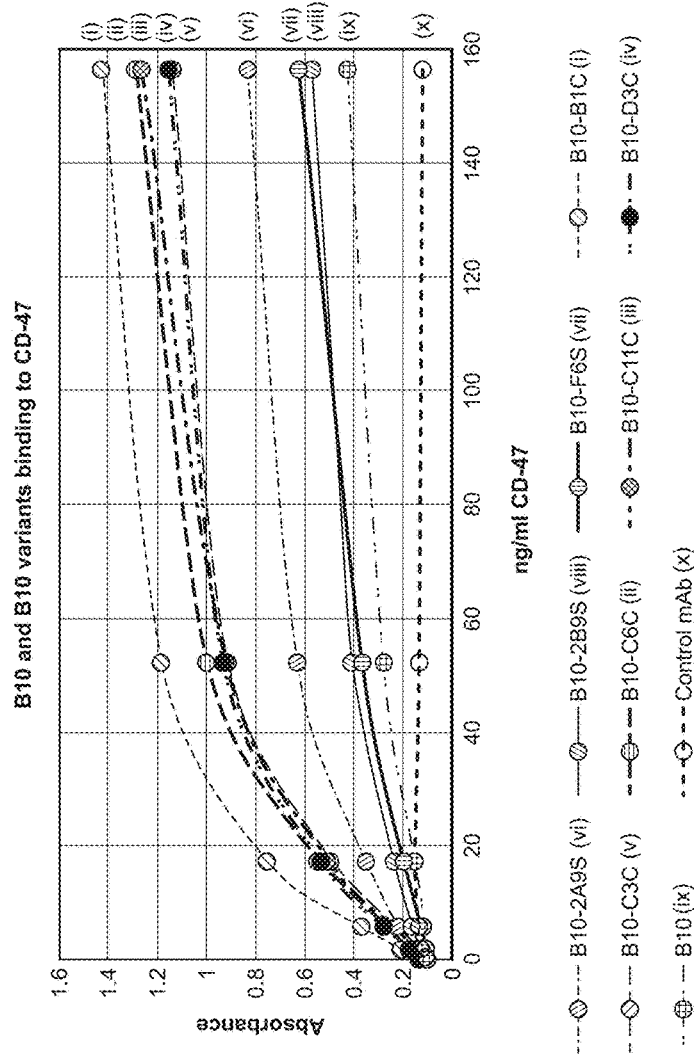
FIG. 4 shows results of an ELISA assay used to determine the binding specificity of antibodies B10 and B10 variants (B10-B1C, B10-C6C, B10-C11C, B10-D3C, B10-C3C, B10-2A9S, B10-F6S, B10-2B-9S) to CD47.

An ELISA was also done to assess the binding of other selected C47B10 variants, i.e., those identified as having higher affinity than parent antibody B10. The ELISA plate was coated with 1 µg/ml goat anti-lambda antibody in PBS overnight at 4° C. The next day it was blocked for 2 h with casein. The antibodies were added at 1 µg/ml in casein and incubated at room temperature for 2.5 h. After washing, serially diluted biotinylated CD47 was added and incubated at room temperature for 1 h. After washing, the plate was incubated with neutravidin-AP for 25 min, then washed, developed with PNPP substrate and the absorbance measured. The results are shown in FIG. 4. The control antibody was an IgG1 that did not bind to the antigen and was used to show that there was not non-specific binding in the assay. As shown in FIG. 4, compared to C47B10, all of the variants that were tested bound more CD47 target, with C47B10-B1C (i), C47B10-C6C (ii), C47B10-C11C (iii), C47B10-DC3 (iv) and C47B10-C3C (v) showing the highest amount of binding of the C47B10 variants that were tested. Under these conditions, the mutated antibodies appear to have stronger binding to antigen compared to C47 B10.

Antibody CD47B10 and CD47A8 and A8 variants C47A8-CS and C47A8-CQ were further studied in BIACORE affinity studies. The affinity of the tested antibodies for human CD47 was determined using surface plasmon resonance (BIACORE). The results of the study are provided below in Table 4.

TABLE 4

| name | ka (1/Ms) | kd (1/s) | KD (M) |
| --- | --- | --- | --- |
| C47A8 | $5.76 \cdot 10^5$ | 0.047 | $8.23 \cdot 10^{-8}$ |
| C47B10 | $1.06 \cdot 10^5$ | $1.29 \cdot 10^{-3}$ | $1.21 \cdot 10^{-8}$ |

TABLE 4-continued

| name | ka (1/Ms) | kd (1/s) | KD (M) |
| --- | --- | --- | --- |
| C47A8-CS | $2.15 \cdot 10^5$ | 0.034 | $1.56 \cdot 10^{-7}$ |
| C47A8-CQ | $1.29 \cdot 10^5$ | 0.02 | $1.56 \cdot 10^{-7}$ |

TABLE 5

Heavy and Light Chain Variable Domain Amino Acid Sequences

| | Heavy chain variable domain regions | Light chain variable domain regions |
| --- | --- | --- |
| C47A8 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO. 1 | QSVLTQPSSVSASPGQSITISCSGT SSDVGGHNYVSWYQQHPGKAP KLMIYDVTKRPSGVPDRFSGSKS GNTASLTVSGLQAEDEADYYCC SYAGSRVYVFGTGTKLTVL SEQ ID NO. 2 |
| C47B10 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO. 1 | QSVLTQPASVSGSPGQSISISCTG TSSDVGGHNYVSWYQQHPGKAP KLMIYDVRNPSGVSNRFSGSKS GSTASLTISGLQTEDEADYYCNS YTGSRTYVFGSGTKLTVL SEQ ID NO. 4 |
| C47B10-1H4S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO. 1 | QSALTQPASVSGSPGQSISISCTG TSVDVGGHNYVSWYQQHPGKA PKLMIYDVRNPSGVSNRFSGSK SGSTASLTISGLQTEDEADYYCN SYTGSRTYVFGSGTKLTVL SEQ ID NO. 5 |
| C47B10-1 (germline changed) | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO: 1 | QSALTQPASVSGSPGQSISISCTG TSSDVGGHNYVSWYQQHPGKAP KLMIYDVRNPSGVSNRFSGSKS GSTASLTISGLQTEDEADYYCNS YTGSRTYVFGSGTKLTVL SEQ ID NO: 8 |
| C47B10-1F6S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO. 1 | QSALTQPASVSGSPGQSISISCTG TSSDVGGHNYVSWYQQHPGKAP KLMIYDVRNPSGVSNRFSGSKS GSTASLTISGLQTEDEADYYCLS YTGSRTYVFGSGTKLTVL SEQ ID NO. 6 |
| C47B10-2A9S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSRLWFSEF DYWGQGTLVTVSS SEQ ID NO. 7 | QSALTQPASVSGSPGQSISISCTG TSSDVGGHNYVSWYQQHPGKAP KLMIYDVRNPSGVSNRFSGSKS GSTASLTISGLQTEDEADYYCNS YTGSRTYVFGSGTKLTVL SEQ ID NO. 8 |
| C47B10-2B11S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSKLWFSEF DYWGQGTLVTVSS SEQ ID NO. 9 | QSALTQPASVSGSPGQSISISCTG TSSDVGGHNYVSWYQQHPGKAP KLMIYDVRNPSGVSNRFSGSKS GSTASLTISGLQTEDEADYYCNS YTGSRTYVFGSGTKLTVL SEQ ID NO. 8 |
| C47B10-2B8S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWYSEF DYWGQGTLVTVSS SEQ ID NO. 10 | QSVLTQPASVSGSPGQSISISCTG TSSDVGGHNYVSWYQQHPGKAP KLMIYDVRNPSGVSNRFSGSKS GSTASLTISGLQTEDEADYYCNS YTGSRTYVFGSGTKLTVL SEQ ID NO. 4 |
| C47B10-2C1S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFTEF DYWGQGTLVTVSS SEQ ID NO. 11 | QSVLTQPASVSGSPGQSISISCTG TSSDVGGHNYVSWYQQHPGKAP KLMIYDVRNPSGVSNRFSGSKS GSTASLTISGLQTEDEADYYCNS YTGSRTYVFGSGTKLTVL SEQ ID NO. 4 |

TABLE 5-continued

Heavy and Light Chain Variable Domain Amino Acid Sequences

| | Heavy chain variable domain regions | Light chain variable domain regions |
|---|---|---|
| C47B10-2B9S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSAF DYWGQGTLVTVSS SEQ ID NO. 12 | QSVLTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL SEQ ID NO. 4 |
| C47B10-2C4S | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSSF DYWGQGTLVTVSS SEQ ID NO. 13 | QSVLTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL SEQ ID NO. 4 |
| C47B10-B1C | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSRLWYTE FDYWGQGTLVTVSS SEQ ID NO. 14 | QSALTQPASVSGSPGQSISISCTG TSVDVGGHNYVSWYQQHPGKA PKLMIYDVRNRPSGVSNRFSGSK SGSTASLTISGLQTEDEADYYCLS YTGSRTYVFGSGTKLTVL SEQ ID NO. 15 |
| C47B10-C6C | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSRLWYTA FDYWGQGTLVTVSS SEQ ID NO. 16 | QSALTQPASVSGSPGQSISISCTG TSVDVGGHNYVSWYQQHPGKA PKLMIYDVRNRPSGVSNRFSGSK SGSTASLTISGLQTEDEADYYCLS YTGSRTYVFGSGTKLTVL SEQ ID NO. 15 |
| C47B10-C3C | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSKLWYTA FDYWGQGTLVTVSS SEQ ID NO. 32 | QSALTQPASVSGSPGQSISISCTG TSVDVGGHNYVSWYQQHPGKA PKLMIYDVRNRPSGVSNRFSGSK SGSTASLTISGLQTEDEADYYCLS YTGSRTYVFGSGTKLTVL SEQ ID NO. 15 |
| C47B10-D3C | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSKLWYTE FDYWGQGTLVTVSS SEQ ID NO. 17 | QSALTQPASVSGSPGQSISISCTG TSVDVGGHNYVSWYQQHPGKA PKLMIYDVRNRPSGVSNRFSGSK SGSTASLTISGLQTEDEADYYCLS YTGSRTYVFGSGTKLTVL SEQ ID NO. 15 |
| C47B10-C11C | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSRLWYSE FDYWGQGTLVTVSS SEQ ID NO. 18 | QSALTQPASVSGSPGQSISISCTG TSVDVGGHNYVSWYQQHPGKA PKLMIYDVRNRPSGVSNRFSGSK SGSTASLTISGLQTEDEADYYCLS YTGSRTYVFGSGTKLTVL SEQ ID NO. 15 |
| C47K11 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO. 1 | DIQLTQSPSTLSASVGDRVTITCR ATQTTNSWLAWYQQKPGKAPK LLIYKASSLDSGVPSRFSGSGSGT EFTLTISSLQPDDFATYYCQQYN GFRMYTFGQGTKLEIK SEQ ID NO. 19 |
| C47KD8 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO. 1 | DIVMTQTPSSLSASVGDRVTITCR ASQSISRYLNWYQQKPGKAPKLL IYAASSLQSGVPSRFSGSGSGTEF TLTISSLQPDDFATYYCQQYNGF RMYTFGQGTKVEIK SEQ ID NO. 20 |
| C47KD9 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO. 1 | DIVMTQSPLSLPVTPGEPASISCR SSQSLLHKNGNNYLDWYLQRPG QSPQLLIYLASNRASGVPDRFSGS GSGTDFTLEISRVQPEDVGVYYC MRGLQTPTFGPGTKVDIK SEQ ID NO. 21 |
| C47B10-H3-D4 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWVSEF DYWGQGTLVTVSS SEQ ID NO: 22 | QSALTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL SEQ ID NO: 8 |

TABLE 5-continued

Heavy and Light Chain Variable Domain Amino Acid Sequences

| | Heavy chain variable domain regions | Light chain variable domain regions |
|---|---|---|
| C47B10-L1A-A10 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO: 1 | QSALTQPASVSGSPGQSISISCTG TSSDVGWHNYVSWYQQHPGKA PKLMIYDVRNRPSGVSNRFSGSK SGSTASLTISGLQTEDEADYYCN SYTGSRTYVFGSGTKLTVL SEQ ID NO: 23 |
| C47B10-H3-D3 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DWWGQGTLVTVSS SEQ ID NO: 24 | QSALTQPASVSGSPGQSISISCTG TSSDVGGHNYVSWYQQHPGKAP KLMIYDVRNRPSGVSNRFSGSKS GSTASLTISGLQTEDEADYYCNS YTGSRTYVFGSGTKLTVL SEQ ID NO: 8 |
| C47B10-L1A-A4 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO: 1 | QSALTQPASVSGSPGQSISISCTG TSSDVVGHNYVSWYQQHPGKAP KLMIYDVRNRPSGVSNRFSGSKS GSTASLTISGLQTEDEADYYCNS YTGSRTYVFGSGTKLTVL SEQ ID NO:25 |
| C47B10-L3-B2 | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO: 1 | QSALTQPASVSGSPGQSISISCTG TSSDVGGHNYVSWYQQHPGKAP KLMIYDVRNRPSGVSNRFSGSKS GSTASLTISGLQTEDEADYYCTS YTGSRTYVFGSGTKLTVL SEQ ID NO: 26 |
| C47A8-CA | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO: 1 | QSVLTQPSSVSASPGQSITISCSGT SSDVGGHNYVSWYQQHPGKAP KLMIYDVTKRPSGVPDRFSGSKS GNTASLTVSGLQAEDEADYYCA SYAGSRVYVFGTGTKLTVL SEQ ID NO: 27 |
| C47A8-CL | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO: 1 | QSVLTQPSSVSASPGQSITISCSGT SSDVGGHNYVSWYQQHPGKAP KLMIYDVTKRPSGVPDRFSGSKS GNTASLTVSGLQAEDEADYYCL SYAGSRVYVFGTGTKLTVL SEQ ID NO: 28 |
| C47A8-CQ | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO: 1 | QSVLTQPSSVSASPGQSITISCSGT SSDVGGHNYVSWYQQHPGKAP KLMIYDVTKRPSGVPDRFSGSKS GNTASLTVSGLQAEDEADYYCQ SYAGSRVYVFGTGTKLTVL SEQ ID NO: 29 |
| C47A8-CS | QVQLVQSGAEVKKPGASVKVSCKASG YTFTSYYMHWVRQAPGQGLEWMGIIN PSGGSTSYAQKFQGRVTMTRDTSTSTV YMELSSLRSEDTAVYYCARSTLWFSEF DYWGQGTLVTVSS SEQ ID NO: 1 | QSVLTQPSSVSASPGQSITISCSGT SSDVGGHNYVSWYQQHPGKAP KLMIYDVTKRPSGVPDRFSGSKS GNTASLTVSGLQAEDEADYYCSS YAGSRVYVFGTGTKLTVL SEQ ID NO: 30 |

INCORPORATION BY REFERENCE

The contents of all references, patents, pending patent applications and published patents, cited throughout this application are hereby expressly incorporated by reference.

We claim:

1. A fully human anti-CD47 antibody, or an antigen-binding fragment thereof, comprising a heavy chain variable domain comprising complementarity determining regions (CDRs) as set forth in a heavy chain variable domain amino acid sequence selected from the group consisting of SEQ ID NO: 1, SEQ ID NO: 7, SEQ ID NO: 9, SEQ ID NO: 10, SEQ ID NO: 11, SEQ ID NO: 12, SEQ ID NO: 13, SEQ ID NO: 14, SEQ ID NO: 16, SEQ ID NO: 17, SEQ ID NO: 18, SEQ ID NO: 22, SEQ ID NO: 24, and SEQ ID NO: 32; and comprising a light chain variable domain comprising CDRs as set forth in a light chain variable region amino acid sequence selected from the group consisting of SEQ ID NO: 2, SEQ ID NO: 4, SEQ ID NO: 5, SEQ ID NO: 6, SEQ ID NO: 8, SEQ ID NO: 15, SEQ ID NO: 19, SEQ ID NO: 20, SEQ ID NO: 21, SEQ ID NO: 23, SEQ ID NO: 25, SEQ ID NO: 26, SEQ ID NO: 27, SEQ ID NO: 28, SEQ ID NO: 29, and SEQ ID NO: 30.

2. The fully human antibody of claim 1, wherein the antibody comprises a heavy chain/light chain variable domain sequence selected from the group consisting of: SEQ ID NO. 1/SEQ ID NO. 2 (C47A8), SEQ ID NO. 1/SEQ ID NO. 4 (C47B10), SEQ ID NO:1/SEQ ID NO:8 (C47B10-1), SEQ ID NO. 1/SEQ ID NO. 5 (C47B10-1H4S), SEQ ID NO. 1/SEQ ID NO. 6 (C47B10-1F6S), SEQ ID NO. 7/SEQ ID NO. 8 (C47B10-2A9S), SEQ ID NO. 9/SEQ ID NO. 8 (C47B10-2B11S), SEQ ID NO. 10/SEQ ID NO. 4(C47B10-2B8S), SEQ ID NO. 11/SEQ ID NO. 4 (C47B10-2C1S), SEQ ID NO. 12/SEQ ID NO. 4(C47B10-2B9S), SEQ ID NO. 13/SEQ ID NO. 4 (2C4S), SEQ ID NO. 14/SEQ ID NO. 15(C47B10-B1C), SEQ ID NO. 16/SEQ ID NO. 15 (C47B10-C6C), SEQ ID NO. 17/SEQ ID NO. 15 (C47B10-D3C), SEQ ID NO. 18/SEQ ID NO. 15 (C47B10-C11C), SEQ ID NO. 19/SEQ ID NO. 15(C47B10-C11C), SEQ ID NO. 1/SEQ ID NO. 20 (C47KD8), SEQ ID NO. 1/SEQ ID NO. 21(C47KD9), SEQ ID NO:1/SEQ ID NO:8 (C47B10-1H4S2), SEQ ID NO. 32/SEQ ID NO. 15(C47B10-C3C), SEQ ID NO. 1/SEQ ID NO. 19 (C47K11), SEQ ID NO:22/SEQ ID NO:8(C47B10-H3-D4), SEQ ID NO:1/SEQ ID NO:23 (C47B10-L1A-A10), SEQ ID NO:24/SEQ ID NO:8 (C47B10-H3-D3), SEQ ID NO:1/ SEQ ID NO:25 (C47B10-L1A-A4), SEQ ID NO:1/SEQ ID NO:26 (C47B10-L3-B2), SEQ ID NO:1/SEQ ID NO:27 (C47A8-CA), SEQ ID NO:1/SEQ ID NO:28 (C47A8-CL), SEQ ID NO:1/SEQ ID NO:29 (C47-A8-CQ), and SEQ ID NO:1/SEQ ID NO:30 (C47A8-CS).

3. The fully human antibody of claim 1, wherein the antibody has a $K_D$ of at least 1×10M.

4. The antigen-binding-fragment of claim 1, wherein the fragment comprises a heavy chain/light chain variable domain sequence selected from the group consisting of: SEQ ID NO. 1/SEQ ID NO. 2, SEQ ID NO. 1/SEQ ID NO. 4, SEQ ID NO. 1/SEQ ID NO. 5, SEQ ID NO:1/SEQ ID NO:8, SEQ ID NO. 1/SEQ ID NO. 6, SEQ ID NO. 7/SEQ ID NO. 8, SEQ ID NO. 9/SEQ ID NO. 8, SEQ ID NO. 10/SEQ ID NO. 4, SEQ ID NO. 11/SEQ ID NO. 4, SEQ ID NO. 12/SEQ ID NO. 4, SEQ ID NO. 13/SEQ ID NO. 4, SEQ ID NO. 14/SEQ ID NO. 15, SEQ ID NO. 16/SEQ ID NO. 15, SEQ ID NO. 17/SEQ ID NO. 15, SEQ ID NO. 18/SEQ ID NO. 15, SEQ ID NO. 1/SEQ ID NO. 20, SEQ ID NO. 1/SEQ ID NO. 21, SEQ ID NO. 1/SEQ ID NO. 22, SEQ ID NO:1/SEQ ID NO:8, SEQ ID NO. 32/SEQ ID NO. 15, SEQ ID NO. 1/SEQ ID NO. 19, SEQ ID NO:22/SEQ ID NO:8, SEQ ID NO:1/SEQ ID NO:23, SEQ ID NO:24/SEQ ID NO:8, SEQ ID NO:1/ SEQ ID NO:25, SEQ ID NO:1/SEQ ID NO:26, SEQ ID NO:1/SEQ ID NO:27, SEQ ID NO:1/SEQ ID NO:28, SEQ ID NO:1/SEQ ID NO:29, and SEQ ID NO:1/SEQ ID NO:30, wherein the fragment is a single chain antibody comprising a peptide linker connecting the heavy and light chain variable domains, or a Fab fragment.

5. The Fab fragment of claim 4, wherein the antibody has a $K_D$ of at least $1\times10^{-6}$ M.

6. A method of treating CD47-associated cancer or a CD47-associated fibrotic disease in a subject in need thereof, the method comprising administering an effective amount of the antibody of claim 2, such that the cancer is treated.

7. The method of claim 6, wherein the cancer is selected from the group consisting of: ovarian cancer, colon cancer, breast cancer, lung cancer, myelomas, neuroblastic-derived CNS tumors, monocytic leukemias, B-cell derived leukemias, T-cell derived leukemias, B-cell derived lymphomas, T-cell derived lymphomas, and mast cell derived tumors.

8. The method of claim 6, wherein the fibrotic disease is selected from the group consisting of myocardial infarction, angina, osteoarthritis, pulmonary fibrosis, asthma, cystic fibrosis, bronchitis, and asthma.

9. A method of treating CD47-associated cancer or a CD47-associated fibrotic disease in a subject in need thereof, the method comprising administering an effective amount of the antibody fragment of claim 4.

10. The method of claim 9, wherein the cancer is selected from the group consisting of: ovarian cancer, colon cancer, breast cancer, lung cancer, myelomas, neuroblastic-derived CNS tumors, monocytic leukemias, B-cell derived leukemias, T-cell derived leukemias, B-cell derived lymphomas, T-cell derived lymphomas, and mast cell derived tumors.

11. The method of claim 9, wherein the fibrotic disease is selected from the group consisting of myocardial infarction, angina, osteoarthritis, pulmonary fibrosis, asthma, cystic fibrosis, bronchitis, and asthma.

12. The antibody, or antigen-binding fragment thereof, of claim 1, which has a $K_D$ of at least $1\times10^{-6}$ M.

13. A pharmaceutical composition comprising the anti-CD47 antibody, or antibody fragment of claim 1, and a pharmaceutically acceptable carrier.

14. A method of treating CD47-associated cancer or a CD47-associated fibrotic disease in a human subject in need thereof, comprising administering an effective amount of the anti-CD47 antibody, or antigen-binding fragment thereof, of claim 1 to the subject, such that cancer or the fibrotic disease is treated.

15. The method of claim 14, wherein the cancer is selected from the group consisting of: ovarian cancer, colon cancer, breast cancer, lung cancer, myelomas, neuroblastic-derived CNS tumors, monocytic leukemias, B-cell derived leukemias, T-cell derived leukemias, B-cell derived lymphomas, T-cell derived lymphomas, and mast cell derived tumors or the fibrotic disease is selected from the group consisting of: myocardial infarction, angina, osteoarthritis, pulmonary fibrosis, asthma, cystic fibrosis, bronchitis, and asthma.

* * * * *

UNITED STATES PATENT AND TRADEMARK OFFICE
CERTIFICATE OF CORRECTION

PATENT NO. : 10,035,855 B2
APPLICATION NO. : 15/061771
DATED : July 31, 2018
INVENTOR(S) : Barbara A. Swanson et al.

It is certified that error appears in the above-identified patent and that said Letters Patent is hereby corrected as shown below:

In the Claims

At Column 85, Claim number 3, Line number 48, insert --$^{-6}$-- after the 10 and before the M.

Signed and Sealed this
Sixteenth Day of April, 2019

Andrei Iancu
*Director of the United States Patent and Trademark Office*